US010935555B2

(12) United States Patent
Salinas et al.

(10) Patent No.: US 10,935,555 B2
(45) Date of Patent: Mar. 2, 2021

(54) DETERMINING CANDIDATE FOR INDUCTION OF LABOR

(71) Applicant: Qiagen Sciences, LLC, Germantown, MD (US)

(72) Inventors: Ruben Salinas, Boston, MA (US); Anthony Ausiello, Boston, MA (US)

(73) Assignee: Qiagen Sciences, LLC, Gaithersburg, MD (US)

(*) Notice: Subject to any disclaimer, the term of this patent is extended or adjusted under 35 U.S.C. 154(b) by 285 days.

(21) Appl. No.: 15/850,813

(22) Filed: Dec. 21, 2017

(65) Prior Publication Data

US 2018/0180625 A1 Jun. 28, 2018

Related U.S. Application Data

(60) Provisional application No. 62/437,945, filed on Dec. 22, 2016.

(51) Int. Cl.
*G01N 33/53* (2006.01)
*G01N 33/68* (2006.01)
(Continued)

(52) U.S. Cl.
CPC ......... *G01N 33/689* (2013.01); *G01N 33/577* (2013.01); *A61B 2010/0074* (2013.01); *G01N 2333/471* (2013.01); *G01N 2800/368* (2013.01)

(58) Field of Classification Search
CPC ............... G01N 33/689; G01N 33/577; G01N 2333/471; G01N 2800/368; A61B 2010/0074
(Continued)

(56) References Cited

U.S. PATENT DOCUMENTS 3,817,837 A 6/1974 Rubenstein et al.
4,313,734 A 2/1982 Leuvering
(Continued)

FOREIGN PATENT DOCUMENTS

AU 2004226798 A1 10/2004
CA 2515205 A1 10/2004
(Continued)

OTHER PUBLICATIONS

Actim Prom, "Qualitative Test for Detection of Amniotic Fluid in the Vagina, Instructions for Use," Medix Biochemica pamphlet, 2004, 1 page.
(Continued)

Primary Examiner — Christopher L Chin
(74) Attorney, Agent, or Firm — Fish & Richardson P.C.

(57) ABSTRACT

A method of determining suitability of a pregnant woman to be a candidate for induction of labor can include: obtaining a vaginal fluid sample from a pregnant woman; contacting the vaginal fluid sample with a PAMG-1 antibody that binds with PAMG-1; detecting whether the PAMG-1 antibody binds with PAMG-1 in the vaginal fluid sample to form a PAMG-1-antibody complex; and providing the determination of suitability for induction of labor to the pregnant woman. When the PAMG-1-antibody complex forms, the pregnant woman is determined to be in a condition that is not suitable for induction of labor because PAMG-1 is detected in the vaginal sample. When the PAMG-1-antibody complex does not form, the pregnant woman is determined to be in a condition that is suitable to be a candidate for induction of labor because the PAMG-1 is not detected in the vaginal sample.

4 Claims, 2 Drawing Sheets

(51) Int. Cl.
    *G01N 33/577*    (2006.01)
    *A61B 10/00*    (2006.01)
(58) Field of Classification Search
    USPC .......................................................... 435/7.1
    See application file for complete search history.

(56) References Cited

U.S. PATENT DOCUMENTS

| | | | |
|---|---|---|---|
| 4,366,241 A | 12/1982 | Tom et al. | |
| 4,373,932 A | 2/1983 | Gribnau et al. | |
| 4,376,110 A | 3/1983 | David et al. | |
| 4,595,661 A | 6/1986 | Cragle | |
| 4,632,901 A | 12/1986 | Valkirs et al. | |
| 4,703,017 A | 10/1987 | Campbell et al. | |
| 4,770,853 A | 9/1988 | Bernstein | |
| 4,806,312 A | 2/1989 | Greenquist | |
| 4,810,658 A | 3/1989 | Shanks et al. | |
| 4,857,453 A | 8/1989 | Ullman et al. | |
| 4,906,439 A | 3/1990 | Grenner | |
| 4,918,025 A | 4/1990 | Grenner | |
| 4,943,522 A | 7/1990 | Eisinger et al. | |
| 4,946,778 A | 8/1990 | Ladner et al. | |
| 4,952,517 A | 8/1990 | Bahar | |
| 4,959,305 A | 9/1990 | Woodrum | |
| 4,978,503 A | 12/1990 | Shanks et al. | |
| 4,981,768 A | 1/1991 | Monbaliu et al. | |
| 5,030,558 A | 7/1991 | Litman et al. | |
| 5,037,735 A | 8/1991 | Khanna et al. | |
| 5,051,237 A | 9/1991 | Grenner et al. | |
| 5,073,484 A | 12/1991 | Swanson et al. | |
| 5,114,673 A | 5/1992 | Berger et al. | |
| 5,132,405 A | 7/1992 | Huston et al. | |
| 5,137,808 A | 8/1992 | Ullman et al. | |
| 5,138,868 A | 8/1992 | Long | |
| 5,141,871 A | 8/1992 | Kureshy et al. | |
| 5,147,609 A | 9/1992 | Grenner | |
| 5,156,952 A | 10/1992 | Litman et al. | |
| 5,186,897 A | 2/1993 | Eason et al. | |
| 5,252,459 A | 10/1993 | Tarcha et al. | |
| 5,284,749 A | 2/1994 | Crowley et al. | |
| 5,308,775 A | 5/1994 | Donovan et al. | |
| 5,352,582 A | 10/1994 | Lichtenwalter et al. | |
| 5,354,692 A | 10/1994 | Yang et al. | |
| 5,476,786 A | 12/1995 | Huston | |
| 5,554,504 A | 9/1996 | Rutanen | |
| 5,559,041 A | 9/1996 | Kang et al. | |
| 5,585,241 A | 12/1996 | Lindnno | |
| 5,597,700 A | 1/1997 | Konstantinov et al. | |
| 5,602,040 A | 2/1997 | May et al. | |
| 5,622,871 A | 4/1997 | May et al. | |
| 5,654,162 A | 8/1997 | Guire et al. | |
| 5,712,172 A | 1/1998 | Huang et al. | |
| 5,714,389 A | 2/1998 | Charlton et al. | |
| 5,728,587 A | 3/1998 | Kang et al. | |
| 5,747,273 A | 5/1998 | Khosravi et al. | |
| 5,807,690 A | 9/1998 | Sanders et al. | |
| 5,877,029 A | 3/1999 | Fuks et al. | |
| 5,891,722 A | 4/1999 | Fuks et al. | |
| 5,968,758 A | 10/1999 | Fuks et al. | |
| 5,989,921 A | 11/1999 | Charlton et al. | |
| 6,020,147 A | 2/2000 | Guire et al. | |
| 6,348,323 B1 | 2/2002 | Khosravi et al. | |
| 6,485,982 B1 | 11/2002 | Charlton | |
| 7,709,272 B2 | 5/2010 | Fuks et al. | |
| 8,114,027 B2 | 2/2012 | Triva | |
| 8,114,610 B2 | 2/2012 | Fuks et al. | |
| 8,765,487 B2 * | 7/2014 | Wallace | G01N 33/558 |
| | | | 436/501 |
| 9,429,580 B2 | 8/2016 | Fuks et al. | |
| 9,494,596 B2 | 11/2016 | Fuks et al. | |
| 9,568,479 B2 | 2/2017 | Fuks et al. | |
| 9,891,233 B2 | 2/2018 | Ausiello et al. | |
| 10,338,065 B2 * | 7/2019 | Wallace | G01N 33/558 |
| 2005/0136490 A1 | 6/2005 | Rutanen | |
| 2006/0240498 A1 | 10/2006 | Fuks et al. | |
| 2009/0269782 A1 * | 10/2009 | Rutanen | G01N 33/689 |
| | | | 435/7.1 |
| 2010/0311190 A1 | 12/2010 | Fuks et al. | |
| 2012/0009609 A1 | 1/2012 | Fuks et al. | |
| 2012/0135432 A1 | 5/2012 | Rutanen | |
| 2013/0071865 A1 | 3/2013 | Fuks et al. | |
| 2014/0011220 A1 | 1/2014 | Fuks et al. | |
| 2014/0234987 A1 | 8/2014 | Ausiello et al. | |
| 2016/0291031 A1 | 10/2016 | Ausiello et al. | |
| 2016/0327565 A1 | 11/2016 | Fuks et al. | |
| 2017/0023582 A1 | 1/2017 | Fuks et al. | |
| 2018/0156814 A1 | 6/2018 | Ausiello et al. | |
| 2018/0180624 A1 | 6/2018 | Salinas | |
| 2018/0180625 A1 | 6/2018 | Salinas | |

FOREIGN PATENT DOCUMENTS

| | | |
|---|---|---|
| CN | 1697972 | 11/2005 |
| CN | 101103931 A | 1/2008 |
| EP | 0143574 | 6/1985 |
| EP | 0229359 | 7/1987 |
| EP | 0316919 | 5/1989 |
| EP | 0362809 | 4/1990 |
| EP | 0281327 | 6/1993 |
| EP | 0560411 | 9/1993 |
| EP | 0280559 | 10/1993 |
| EP | 0299428 | 1/1996 |
| EP | 0565541 | 12/1997 |
| EP | 1608268 A1 | 12/2005 |
| JP | 2004/528036 | 9/2004 |
| JP | A-2005-535887 | 11/2005 |
| JP | 2007523663 A | 8/2007 |
| JP | A-2010-518058 | 5/2010 |
| NZ | 541560 A | 9/2009 |
| RU | 1614194 | 5/1998 |
| RU | 2110800 | 5/1998 |
| WO | WO 1989/012690 | 12/1989 |
| WO | WO 1992/012426 | 7/1992 |
| WO | WO 1988/008534 | 11/1998 |
| WO | WO 1999/046597 | 9/1999 |
| WO | WO 2004/014220 | 2/2004 |
| WO | WO 2008/096122 | 8/2008 |
| WO | 2009018607 A1 | 2/2009 |
| WO | WO 2009/018607 | 2/2009 |
| WO | WO 2010/020043 | 2/2010 |

OTHER PUBLICATIONS

Alexander et al., "Clinical course of premature rupture of the membranes" Seminars in Perinatology, 1996, 20(5):369-374.

Allander, et al., "The Proceedings of the 2nd International Workshop of IGF Binding Proteins, Aug. 27-30, 1992, Opio, Cote d'Azur, France, Growth Regulation: Gene Structures and Expressions, Structure and Chromosomal Localization of Human Insulin-like Growth Factor-Binding Protein Genes," 1998, pp. 3-5.

AmniSure® ROM (Rupture of [fetal] Membranes) Test, Directions for In Vitro Diagnostic Use, 2 pages, (2010).

Australian Office Action in Application No. 2013371462, dated Jul. 26, 2018, 4 pages.

Ballard, et al., "Report on the Nomenclature of the IGF Binding Proteins," Journal of Clinical Endocrinology and Metabolism, 1990, 70(3): 817-818.

Bell, S. C., "Secretory endometrial and decidual proteins: studies and clinical significance of a maternally derived group of pregnancy-associated serum proteins," *Human Reproduction*, 1986, 1(3):129-143.

Bell et al., "N-Terminal Amino Acid Sequence of Human Pregnancy-Associated Endometrial a1-Globulin, an Endometrial Insulin-like Growth Factor (IGF) Binding Protein—Evidence for Two Small Molecular Weight IGF Binding Proteins," Endocrinology, 1988, 123(2):1202-4.

Bell, "Regulation of Insulin-Like Growth Factor-Binding Protein-1 Synthesis and Secretion by Progestin and Relaxin in Long Term Cultures of Human Endometrial Stromal Cells," Journal of Clinical Endocrinology and Metabolism, 1991, 72(5):1014-1024.

(56) References Cited

OTHER PUBLICATIONS

Bell, "Monclonal Antibodies to Human Secretory Pregnancy-Associated Endometrial a1-Blobulin, an Insulin-Like Growth Factor Binding Protein: Characterization and Use in Radioimmunoassay, Western Blots, and Immunohistochemistry," American Journal of reproductive Immunology, 1989, 20:87-96.

Berggard et al., Histologic Distribution and Biochemical Properties of α1- Microglobulin in Human Placenta. American Journal of Reproductive Immunology 41:52-60.

Berggard et al., "Structure and distribution of alpha-1-microglobulin proteins," Doctoral Dissertation, Lund University, Faculty of Medicine, Oct. 31, 1998, 4 pages (abstract).

Bischof, "The Pregnancy Proteins (PP12. PP14 and PAPP-A): Their Biological and Clinical Relevance," American Journal of Perinatology, 1989, 6(2):110-116.

Bohn, "The Human Placenta: Proteins and Hormones," Proceedings of the Serno Symposia, 1980, 35:23-34.

Bohn et al., "Isolation and Characterization of a New Placenta Specific Protein (PP12)," Arch. Gynecol., 1980, 229:279-291.

Bohn et al., "New Soluble Placental Tissue Proteins: Their Isolation, Characterization, Localization and Quantification." Immunology of Human Placental Proteins, 1982, pp. 67-81, supplement 4.

Boltovskaia, M.N. et al. Biull. Eksp. Biol. Med., (1991) 112(10): 397-400[1] (Russian) (not attached) Boltovskaia, M.N. et al. Experimental Biology and Medicine (1992) 112(10): 1457-1460 (English).

Boltovskaya et al., "Histochemical and Clinical-Diagnostic Study of Placental α1-Microglobulin Using Monoclonal Antibodies", Laboratory of Cellular Immunopathology and Biotechnology, Institute of Human Morphology, Academy of Medical Sciences of the USSR. Laboratory of Immunology, Moscow. Translated from Byulleten' Eksperimental'noi Biologii i Meditsiny, vol. 112, No. 10, pp. 397-400, Oct. 1991. Original article submitted Mar. 29, 1991.

Brazilian Office Action in Application No. BR 1220170218190, dated Jun. 5, 2018, 8 pages (with English translation).

Brazilian Office Action in Application No. BR 1220170218190, dated May 21, 2019, 9 pages (with English translation).

Brazilian Office Action in Application No. BR 1120150160271, dated Aug. 27, 2019, 7 pages (with English summary).

Briese et al., "Circulating Levels of Placental Protein 12 (PP 12) in Diabetic Pregnancy Complicated by Retinopathy," Exp. Clin. Endocrinol., 1990, 95(1):105-109.

Burdett et al., "Proteins of human amniotic fluid. II. Mapping by two-dimensional electrophoresis," Clinical Chem., Apr. 1982, 28(4):935-940 (abstract).

Busby et al., "Purification of a 31,000-dalton insulin-like growth factor binding protein from human amniotic fluid: Isolation of two forms with different biologic actions," J. Biol. Chem., 1988, 263(28):14203-10.

Canadian Examiner's Report for Application Serial No. 2,533,915, dated Apr. 3, 2017, 3 pages.

Canadian IPO Search Report for Canadian counterpart Application Serial No. 2,533,915, dated Apr. 14, 2010, 5 pages.

Canadian Office Action in Application No. 2,897,053, dated May 10, 2018, 4 pages.

Chen, et al., "Comparison of two rapid strip tests based on IGFBP-1 and PAMG-1 for the detection of amniotic fluid," Amer. J. Perinatology, 2008, 25(4):243-246.

Cote et al., "Generation of human monoclonal antibodies reactive with cellular antigens," Proc. Natl. Acad. Sci. US.A. 1983, 80:2026-2030.

Cousins et al., "AmniSure Placental Alpha Microglobulin-1 Rapid Immunoassay versus Standard Diagnostic Methods for Detection of Rupture of Membranes," Am J Perinatol., 2005, 22:1-5.

Crowe, C., "AmniSure; (placental alpha-I microglobulin) Rupture of Fetal Membrane Test", http://webserver.pa-ucl.com/wwwdocs/analyticalproc/FrameA.htm, Mar. 31, 2012, (3 pages).

Cubbage et al., "Structure of the Human Chromosomal Gene for the 25 Kilodalton Insulin-Like Growth Factor Binding Protein," Molecular Endocrinology, 1989, 3:35:846-851.

Darj et al., "Insulin-like growth factor binding protein-1, a quick way to detect amniotic fluid," Acta. Obstet. Gynecol. Scand., 1998, 77:295-297.

Database search for PAMG-1. Database accessed Aug. 12, 2013, 1 page.

de Haan et al., "Value of the fern test to confirm or reject the diagnosis of ruptured membranes in modest in nonlaboring women presenting with nonspecific vaginal fluid loss" Am J Perinatol, 1994,11:46-50.

Declaration under 37 C.F.R. 1.132 by Dr. Boris Fuks, dated Apr. 23, 2012 (36 pages).

Declaration under 37 C.F.R. 1.132 by Michael Friedman, dated Jun. 21, 2011 (9 pages).

Diamandi et al., "Immunoassay of Insulin-Like Growth Factor-Binding Protein-3 (IGFBP-3): New means to Quantifying IGFBP-3 Proteolysis," Journal of Clinical Endocrinology and Metabolism, 2000, 85(6):2327-2333.

DiRenzo, et al., "Guidelines for the management of spontaneous preterm labor: identification of spontaneous preterm labor, diagnosis of preterm premature rupture of membranes, and preventive tools for preterm birth," *The Journal of Maternal-Fetal and Neonatal Medicine,* 2011, Early Online, 1-9.

Ehrenborg et al., "Congiguous Localization of the Genes Encoding Human Insulin-like Growth Factor Binding Proteins 1(IGBP1) and 3(IGBP3) on Chromosone 7," Genomics, 1992, 12(3):497-502.

EPO Opposition Division's Decision rejecting the Opposition against EP 2204654, dated Mar. 26, 2015, 15 pages.

Eriksen et al., "Fetal fibronectin: a method for detecting the presence of amniotic fluid," Obstet Gynecol., 1992, 80(3 Pt 1):451-4 (abstract).

European Office Action for Application No. EP13870051.3, dated Jun. 23, 2017, 6 pages.

European Office Action in Application No. EP13870051.3, dated Mar. 1, 2018, 4 pages.

Expert Opinion in the lawsuit 41 O 331/03, May 20, 2005; 12 pages English translation from German.

Extended European Search Report for Application No. 13870051.3 dated Oct. 12, 2016, 4 pages.

Gaucherand et al., "Comparative study of three vaginal markers of the premature rupture of membranes. Insulin like growth factor binding protein 1 diamine-oxidase pH," Acta Obstet Gynecol Scand., 1997, 76(6):536-40.

Giudice, "Multifaceted roles for IGFBP-1 in human endometrium during implantation and pregnancy," Ann N Y Acad Sci., 1997, 828:146-56.

Guibourdenche, et al., "Rapid detection of insulin-like growth factor binding protein-1 and foetal fibronectin in cervico-vaginal secretions to diagnose premature membrane rupture," Ann Clin Biochem., 1999, 36 ( Pt 3):388-90.

Harry et al. "Comparison of physical characteristics and collection and elution performance of clinical swabs." 1\frican Journal of Microbiology Research, Aug. 2, 2013, 7(31), pp. 4039-1048.

Hellemans, "Preliminary results with the use of the ROM-check immunoassay in the early detection of rupture of the amniotic membranes," European Journal of Obstetrics & Gynecology and Reproductive Biology, 1992, 43:173-179.

Indian Examination Report in Indian counterpart Application Serial No. 5175/DELNP/2007, dated Jul. 27, 2010, 3 pages.

International Search Report and Written Opinion in International Application No. PCT/US2013/77541, dated Mar. 21, 2014, 11 pages.

Jain et al., "A clinical study to evaluate the usefulness of the MAST test in diagnosing pre labor rupture of membranes," J Obstet Gynaecol. Jan. 1998;18(1):33-6.

Japanese Examination Report in Japanese counterpart Application Serial No. 2004-528036, dated Feb. 2, 2010, 6 pages (with English Translation).

Japanese Office Action in International Application No. JP2015-551719, dated Aug. 28, 2018, 2 pages (English translation).

Japanese Office Action in International Application No. JP2015-551719, dated Oct. 17, 2017, 4 pages (English Translation).

(56) References Cited

OTHER PUBLICATIONS

Jeurgens-Borst et al., "Use of insulin like growth factor binding protein-1 in the diagnosis of ruptured fetal membranes," European Journal of Obstetrics & Gynecology and Reproductive Biology, 2002, 102:11-14.
Kim et al., "Identification of a family of low-affinity insulin-like growth factor binding proteins (IGFBPs): Characterization of connective tissue growth factor as a member of the IGFBP superfamily," Proc. Natl. Acad. Sci., 1997, 94(24):12981-6.
Kishida et al., "Diagnosis of premature rupture of the membranes in preterm patients, using an improved AFP kit: comparison with ROM-check and/or nitrazine test," European Journal of Obstetrics & Gynecology and Reproductive Biology, 1996, 69:77-82.
Koistinen et al., "Placental Protein 12 Is a Decidual Protein that Binds Somatomedin and Has an Identical NK-Terminal Amino Acid Sequence with Somatomedin-Binding Protein from Human Amniotic Fluid," Endocrinology, 1986, 118(4):1375-1378.
Koninckx et al., "Prolactin Concentration in Vaginal Fluid: A New Method for Diagnosing Ruptured Membranes," British Journal of Obstetrics and Gynecology, 1981, 88:607-610.
Kubota et al., "Evaluation of Insulin-Like Growth Factor Binding Protein-1 as a Diagnostic Tool for Rupture of the Membranes," J. Obstet. Gynaecol. Res., 1998, 24(6)411417.
Ladfors, "Is the use of IGFB-1 for diagnosing ROM of any clinical value" Acta Obstet Gynecol Scand., 1999, 78(6):557-8.
Lee et al., "Comment and reply on: the clinical significance of a positive Amnisure test in women.with term labor with intact membranes," Letters to the editor, The Journal of Maternal-Fetal and Neonatal Medicine, 2010, Early Online, 1-3.
Lee et al, "The clinical significance of a positive Amnisure test TM in women with term, labor with intact membranes," The Journal of Maternal-Fetal and Neonatal Medicine, 2009, 22(4):305-310.
Lee et al. "The clinical significance of a positive Amnisure test in women with preterm labor and intact membranes" The Journal of Maternal-Fetal and Neonatal Medicine, 2012, 25(9), pp. 1690-1698. DOI: 10.3109/14767058.2012.657279.
Lee et al. "The clinical significance of a positive Amnisure test in women with term labor with intact membranes", Author Manuscript. Published in final edited form as: J Matern Fetal Neonatal Med., Apr. 22, 2009(4):305-310.
Lee et al., "Intra-amniotic inflammation in patients with a positive Amnisure test in preterm labor and intact membranes," Am J Obstet Gynecol., Supplemental to Jan. 2012, 204(1):S209.
Lee et al., "Measurement of Placental Alpha-Microglobulin-1 in Cervicovaginal Discharge to Diagnose Rupture of Membranes," Obstet Gynecol., 2007, 109:634-640.
Lee et al., "The clinical significance of a positive Amnisure test in women with preterm labor and intact membranes," J Matern Fetal Neonatal Med., Sep. 2012, 25(9):1690-1698.
Lee et al., "Insulin-Like Growth Factor (IGF) Binding Protein Complementary Deoxyribonucleic Acid from Human HEP G2 Hepatoma Cells: Predicted Protein Sequence Suggests an IGF Binding Domain Different from Those of the IGF-I and IGF-II Receptors," Molecular Endocrinology, 1988, 2(5):404-411.
Letter from Drs. Boris B. Fuks, M.D., Ph.D. and Alexander B. Konstantinov, Ph.D. to European Patent Office (signed Jun. 14, 2005), 2 pages.
Letter from Drs. Boris B. Fuks, M.D., Ph.D. and Alexander B. Konstantinov, Ph.D. to European Patent Office (signed Nov. 30, 2005), 1 page.
Lockwood et al., "Fetal Fibronectin in Cervical and Vaginal Secretions as a Predictor of Preterm Delivery," New England Journal of Medicine, 1991, 325(1):669-674.
Lockwood et al., "Fetal membrane rupture is associated with the presence of insulin-like growth factor-binding protein-1 in vaginal secretions," Am. J. Obstet. Gynecol., 1994, 171(1):146-50.
Loukovaara et al., "Serum insulin-like growth factor-I and insulin-like growth factor binding protein-3 in premature rupture of membranes," Acta Obstet Gynecol Scand. Oct. 2002;81(10):905-8.

Luthman et al., "Human insulin-like growth-factor-binding protein. Low-molecular-mass form: protein sequence and cDNA cloning," Eur. J. Biochem., 1989, 180:259-265.
Marcellin, et al., Analyse comparative de deux tests diagnostiques de rupture prematuree des membranes dans les secretions cervicovaginates, Journal de Gynegologie Obstetrique de la Reproduction, vol. 622:1-6, (2011) English translation.
Marinaro et al., "O-glycosylation delays the clearance of human IGF-binding protein-6 from the circulation," European Journal of Endocrinology, 2000, 142:512-516.
Medix Biochemica. 2006. Actim PROM (product information), 1 page.
Mercer et al. "The Preterm Prediction Study: prediction of preterm premature rupture of membranes through clinical findings and ancillary testing," The NICHD Maternal-Fetal Medicine Units Network. Am J Obstet Gynecol., 2000;183:738-745.
Mercer, "Preterm Premature rupture of the membranes," Obstet Gynecol, 2003, 101:178-193.
Mittal et al., "A role for placental alpha-microglobulin-1 in the identification of women with a sonographic short cervix at risk for spontaneous rupture of membranes," Am J Obstet Gynecol., 2010, 196 (Supplement to Dec. 2009):528.
Morrison et al., "Isolation of transformation-deficient *Streptococcus pneumoniae* mutants defective in control of competence, using insertion-duplication mutagenesis with the erythromycin resistance determinant of pAM beta 1," J. Bacteriol., 1984, 159:870-876.
Nasimova et al., "The content of the PAMG-1 protein that binds insulin-like growth factor I (somatomedin C) in the blood serum of diabetic patients," The Bulletin of Experimental Biology and Medicine, 1993, 116(9):302-304 (with English abstract).
Nikolova et al. "Comparison of a novel test for placental alpha microglobulin-1 with fetal fibronectin and cervical 5 length measurement for the prediction of imminent spontaneous preterm delivery in patients with threatened preterm abor." J_ Perina. Med., 2015. DOI: 10.1515/jpm-2014-0300.
Nikolova et al. "Evaluation of a novel placental alpha microglobulin-1 (PAMG-1) test to predict spontaneous preterm delivery." J_ Perina., Med., 2013.
Nilsson et al., "Explorative Study of the Protein Composition of Amniotic Fluid by Liquid Chromatography Electrospray Ionization Fourier Transform Ion Cyclotron Resonance Mass Spectrometry," Journal of Proteome Research, 2004, 3(4):884-889.
Nisell et al., "Assessment of fetal fibronectin in cervical secretion in cases of equivocal rupture of the membranes at term," Acta Obstet Gynecol Scand., 1996, 75(2):132-4.
Notice of Opposition dated Sep. 18, 2013 for Application No. 10160487.4-1408 / 2204654, 31 pages.
Notification to Attend Oral Proceedings in the Opposition filed against EP 2204654, dated Jul. 24, 2014, 19 pages.
Ooi et al., "Recognition of insulin-like-growth-factor-binding proteins in serum and amniotic fluid by an antiserum against a low-molecular-mass insulin-like-growth-factor-inhibitor/binding protein," Biochem. J., 1990, 267:615-620.
Paternoster et al., "Comparative analysis of premature labor markers," Acta Biomed Ateneo Parmense, 2000, 71 Suppl 1:331-6 (with English abstract).
Pekonen et al. "A Monoclonal Antibody-Based Immunoradiometric Assay for Low Molecular Weight Insulin-Like Growth Factor Binding Protein/Placental Protein 12," Journal of Immunoassay, 1989, pp. 325-337.
Petrunin et al., "The Immunochemical Identification of Organ-Specific α-1 Globulin of the Human Placenta and its Content in the Amniotic Fluid," Bulletin of Experimental Biology and Medicine, 1977, 5:558 (with English translation).
Petrunin et al., "Regarding PAMG," 1990, 1:369-77 (English Abstract Only).
Petrunin et al., "A Comparative Study of Four Human Placental Proteins in the Course of Pregnancy," 1988, 50-52 (English abstract on p. 52).
Pollet-Villard et al. "Detection of Placental Alpha Microglobulin-1 versus Insulin-Like Growth Factor-Binding Protein-1 in Amniotic Fluid at Term: A Comparative Study," Amer J Perinatol, 2011, 28(6):489-94.

(56) References Cited

OTHER PUBLICATIONS

Povoa et al., "Cross-reaction of serum somatomedin-binding protein in a radioimmunoassay developed for somatomedin-binding protein isolated from human amniotic fluid," Acta Endocrinologica, 1984, 107:563-570.
Ragosch, et al. "Insulin like growth factor binding protein 1 (IGFBP-1) and Fetales Fibronectin in der Diagnostik Eines Verzeitigen Blasensprunges," Geburtshilfe. U. Frauenheililk., 1996, 56:291-296 (with English abstract).
Reply to Notice of Opposition filed against EP 2204654, dated Apr. 28, 2014 (81 pages).
Report on the nomenclature of the IGF binding proteins, Journal of Clinical Endocrinology and Metabolism, 1990, 70(3):2.
Request for furnishing samples of deposited microorganisms, 2007, 12 pages.
Rochelson et al., "A Rapid Colorimetric AFP Monoclonal Antibody Tet for the Diagnosis of Preterm Rupture of the Membranes," Obstetrics & Gynecology, 1987, 69(2):163-163.
Rochelson et al., "Rapid Assay—Possible Application in the Diagnosis of Premature Rupture of the Membranes." Obstetrics & Gynecology, Oct. 1983, 62(4):414418.
Romero et al., "Clinical chorioamnionitis is characterized by changes in the expression of the alarmin HMGB1 and one of its receptors, sRAGE," J Matern Fetal Neonatal Med., 2012, 25(6):558-67.
Rosenfeld et al., "The Insulin-like Growth Factor Binding Protein Superfamily: New Perspectives," Pediatrics, 1999, 104:1018-1021.
Rutanen et al., "Radioimmunoassay of Placental Protein 12: Levels in Amniotic Fluid, Cord Blood, and Serum of Healthy Adults, Pregnant Women, and Patients with Trophoblastic Disease," Am. J. Obstet Gynecol., Oct. 15, 1982, 144(4):460-463.
Rutanen et al., "Synthesis of Placental Protein 12 by Human Decidua," Endocrinology, 1985, 116(4):1304-1309.
Rutanen et al., "Diagnosis of Premature Rupture of Fetal Membranes by the Measurement of Insulin-like Growth Factor Binding Protein-1 in Cervical Secretion," Am. J. Obst. Syn., 1991, 164(1)38:258 (abstract).
Rutanen et al., "Evaluation of a rapid strip test for insulin-like growth factor binding protein-1 in the diagnosis of ruptured fetal membranes," Clinica Chimica Acta, 1996, 253:91-101.
Rutanen et al., "Monoclonal Antibodies to the 27-34K Insulin-like Growth Factor Binding Protein," Biochemical and Biophysical Research Communications, 1988, 152(1):208-215.
Rutanen et al., "Measurement of insulin-like growth factor binding protein-1 in cervical/vaginal secretions: comparison with the ROM-check Membrane Immunoassay in the diagnosis of ruptured fetal membranes," Clinica Chimica Acta, 1993, 214:73-81.
Seppälä et al., "Uterine endocrinology and paracrinotogy: insulin-like growth factor binding protein-1 and placental protein 14 revisited," Human Reproduction, 1994, 9(5):917-925.
Seppala et al., "Immunologic and Biological Properties and Clinical Significance of Placental Proteins P135 and PP12," Annals New York Academy of Sciences, 1983, 417:368-382.
SIPO—Office Action in corresponding CN Application No. 201380074274.9, dated Mar. 10, 2016 (12 pages).
Smith, "A technique for the detection of rupture of the membranes: a review and preliminary report," Obstet Gynecol., 1976, 48:172-6.
Statement from VTT Technical Research Centre of Finland, Jun. 26, 2003, 1 page.
Supplement to the Expert Opinion in the lawsuit 41 O 331/03, Dec. 11, 2005; 21 pages, English translation from German.
Tagore, et al., Comparative analysis of insulin-like growth factor binding protein-1 (IGFBP-1), placental alpha-microglobulln-1 (PAMG-1) and nitrazine test to diagnose premature rupture of membranes in pregnancy, J. Perinat. Med., vol. 38:1-4 (2010).
Tatarinov, et al., Placental alphal-microglobulin is a protein that binds somatomedins, pp. 369-378 (1990) English translation.
Tatarinov et al., "Two New Human Placenta-Specific α-Globulines: Identification, Purification, Characteristics, Cellular Localization and Clinical Investigation," Scrono Symposium No. 1980, 35:35-46.
Thomasino et al., "Diagnosing Rupture of Membranes Using Combination Monoclonal/Polyclonal Immunologic Protein Detection," The Journal of Reproductive Medicine, 2013, vol. 58(5-6);187-194.
Tkachenko et al., "Immunochemical studies of the system of specific proteins of the human placenta," Vestn. Ross. Akad. Med. Nauk., 1995 3: 40-44 (Abstract).
UniProtKB/Swiss-Prot database entry for IGFBP-1 (last accessed on Jan. 28, 2012 at http://www.uniprot.org/uniprot/P08833), 10 pages.
Verhaeghe et al., "Regulation of insulin-like growth factor-I and insulin-like growth factor binding protein-1 concentrations in preterm fetuses," Am J Obstet Gynecol., 2003, 188(2):485-91.
Heterogeneous Enzyme-Immunoassays and Their Applications, Voller, 1980, Chapter 9, pp. 181-196.
Woltmann et al., "Detection of Ruptured Fetal Membranes using Insulin-like Growth Factor-binding Protein-1," Z. Geburtsh. Neonatol., 1995, 199:243-244 (with English abstract).
Woyton et al., "Insulin-like growth factor binding protein 1 (IGFBP-1) in vaginal secretion as a marker of premature rupture of amniotic membranes," Ginekol Pol., 1999, 70(11):809-14 (with English summary).
Zaraysky et al., "Immunoenzyme Assay of Placenta Specific .a1-Microglobulin in Donor Blood Serum," Voprosy Med. Khemii, 1989, 5:130-132 (with English abstract).
Zenobi, et al., "Ion formation in MALDI mass spectrometry," Mass Spectrom. Rev., 1998, 17:337-366.
Lee et al. "The clinical significance of a positive Amnisure test in women with term labor with intact membranes". Author Manuscript. Published in final edited form as: J Matern Fetal Neonatal Med., Apr. 2009, 22(4), pp. 305-310. DOI: 10.1080/14767050902801694.
Harry et al. "Comparison of physical characteristics and collection and elution performance of clinical swabs." African Journal of Microbiology Research, Aug. 2, 2013, 7(31), pp. 4039-1048. DOI: 10.5897/AJMR12.1785.
Nikolova et al. "Evaluation of a novel placental alpha microglobulin-1 (PAMG-1) test to predict spontaneous preterm delivery." J. Perinat. Med., 2013. DOI: 10.1515/jmp-2013-0234, 2013.
Nikolova et al. "Comparison of a novel test for placental alpha microglobulin-1 with fetal fibronectin and cervical length measurement for the prediction of imminent spontaneous preterm delivery in patients with threatened preterm labor." J. Perinat. Med., 2015. DOI: 10.1515/jpm-2014-0300.

* cited by examiner

DETERMINING CANDIDATE FOR INDUCTION OF LABOR

CROSS-REFERENCE

This patent application claims priority to U.S. Provisional Application No. 62/437,945 filed Dec. 22, 2016, which provisional is incorporated herein by specific reference in its entirety.

BACKGROUND

In some instances, pregnancy does not naturally progress to childbirth. Accordingly, induction of labor (IOL) has become a common procedure that attempts to move the pregnancy into to active labor. However, not all pregnant women are candidates for IOL for various reasons. In some pregnant women, the IOL procedure can be problematic with significant health risks.

Therefore, it would be advantageous to have improved methods and systems to determine whether or not a pregnant woman is a suitable candidate for IOL.

SUMMARY

In one embodiment, a method of determining suitability of a pregnant woman to be a candidate for induction of labor (IOL) can include: obtaining a vaginal fluid sample from a pregnant woman; contacting the vaginal fluid sample with a PAMG-1 antibody that binds with PAMG-1; and detecting whether the PAMG-1 antibody binds with PAMG-1 in the vaginal fluid sample to form a PAMG-1-antibody complex. When the PAMG-1-antibody complex forms, the pregnant woman is determined to be in a condition that is not suitable for induction of labor because PAMG-1 is detected in the vaginal sample, or when the PAMG-1-antibody complex does not form, the pregnant woman is determined to be in a condition that is suitable to be a candidate for induction of labor because the PAMG-1 is not detected in the vaginal sample. In one aspect, the method can include contacting the vaginal fluid sample with at least two PAMG-1-specific monoclonal antibodies, wherein at least one of the antibodies binds to PAMG-1 when present in the sample to form a PAMG-1/monoclonal antibody complex. In one aspect, the method can include detecting the presence of the PAMG-1/monoclonal antibody complex only when the concentration of PAMG-1 in the vaginal sample is at or exceeds a predefined detection threshold. In one aspect, the method can include detecting the presence of the PAMG-1/monoclonal antibody complex only when the concentration of PAMG-1 in the vaginal sample is at or exceeds a predefined detection threshold of 4 ng/ml. In one aspect, the method can include predicting that the pregnant woman will go into labor without the induction of labor if PAMG-1 is detected in the vaginal sample, or predicting that the pregnant woman will not go into labor without the induction of labor if PAMG-1 is not detected in the vaginal sample. In one aspect, the method can include determining that fetal membranes of the pregnant woman are intact. If intact, the pregnant woman is a candidate for induction of labor. If not intact, the pregnant woman is not a candidate for induction of labor.

In one embodiment, the method can include recommending that the pregnant woman not have induction of labor if PAMG-1 is detected in the vaginal sample, or recommending that the pregnant woman not have induction of labor if PAMG-1 is not detected in the vaginal sample. In one aspect, the method can include providing information regarding induction of labor to the pregnant woman if PAMG-1 is not detected in the vaginal fluid sample. In one aspect, the method can include informing the pregnant woman she is not suitable for induction of labor if PAMG-1 is detected in the vaginal fluid sample. In one aspect, the method can include selecting the pregnant woman to be suitable for induction of labor when the pregnant woman is past term.

In one embodiment, the method can include collecting the vaginal fluid sample from the pregnant woman with a collection device. In one aspect, the collection device is a flocked swab. In one aspect, the collection device is a nylon flocked swab. In one aspect, the collection device is a flocked swab having one or more of: length of shaft being 170.0 mm±1 mm; length of the fiber tip being 22 mm±3 mm; flocked tip diameter being 7.00 mm±1.5 mm; and total length being 171 mm±2 mm from end of shaft to fiber tip. In one aspect, the flocked swab provides a 1:4 dilution of any PAMG-1 present in the vaginal fluid sample. In one aspect, the method can include collecting the vaginal fluid sample with the flocked swab over a time period of about 30 seconds or less.

In one embodiment, the method can include contacting the collection device with a solvent to release PAMG-1 from the collected vaginal fluid sample. In one aspect, the method can include comprising contacting the collection device with the solvent for about 30 seconds or less after collecting the vaginal fluid sample. In one aspect, the vaginal fluid sample is contacted with the at least two PAMG-1-specific monoclonal antibodies for about 5 minutes or less.

In one embodiment, a predefined detection threshold level of PAMG-1 is 4 ng/ml in the vaginal sample for detecting whether the PAMG-1 antibody binds with PAMG-1 to form the PAMG-1-antibody complex. In one aspect, PAMG-1 is determined to be present in the vaginal fluid at or above about 4 ng/ml. In one aspect, PAMG-1 is determined to be absent from the vaginal sample even if present at less than 4 ng/ml. In one aspect, the pregnant woman is determined to be not suitable for induction of labor when PAMG-1 is determined to be present at or above the predefined detection threshold. In one aspect, the pregnant woman is determined to be suitable for induction of labor when PAMG-1 is determined to be absent or below the predefined detection threshold.

In one embodiment, the method can include selecting the pregnant woman to obtain the vaginal fluid sample from based on one or more criteria. In one aspect, the one or more criteria include: woman with an uncomplicated pregnancy at least at term gestation; woman of South Asian and Afro-Caribbean origin at least at 40 weeks gestation; woman that is at least 40 years old at least at 40 weeks gestation; woman with preterm prelabour rupture of membranes (PPROM) at least at 34 weeks gestation; woman with prelabour rupture of membranes (PROM) at least at 37 weeks gestation; woman with an estimated fetal weight (EFW) below 5th percentile after 37 weeks gestation but normal amniotic fluid and Doppler results; woman with fetal growth restriction (FGR) at least at 34 weeks gestation; woman with insulin-dependent diabetes mellitus (DM) at least at 38 weeks gestation; woman with gestational diabetes mellitus (GDM) at least at 40 weeks gestation; woman with chronic hypertension/gestational hypertension at least at 37 weeks gestation; woman with preeclampsia at least at 34 weeks gestation; woman with an uncomplicated dichorionic diamniotic (DCDA) twin pregnancy at least at 38 weeks gestation; woman with reduced fetal movements (RFM) at least at 37 weeks gestation; woman with signs of infection, bleeding or spontaneous rupture of membrane (SROM) gestation;

woman with previous lower segment caesarean section at least at 40 weeks gestation; or woman with severe symphysis pubis dysfunction at least at 38 weeks gestation.

In one aspect, the pregnant woman having the PAMG-1 below the predefined detection threshold is suitable for induction of labor when also having one or more of the following criteria: woman with an uncomplicated pregnancy at least at term plus 7 days; woman of South Asian and Afro-Caribbean origin at least at 40 weeks gestation; woman that is at least 40 years old at least at 40 weeks gestation; woman with preterm prelabour rupture of membranes (PPROM) at least at 34 weeks gestation; woman with prelabour rupture of membranes (PROM) at least at 37 weeks gestation; woman with an estimated fetal weight (EFW) below 5th percentile after 37 weeks gestation but normal amniotic fluid and Doppler results; woman with fetal growth restriction (FGR) at least at 34 weeks gestation; woman with insulin-dependent diabetes mellitus (DM) at least at 38 weeks gestation; woman with gestational diabetes mellitus (GDM) at least at 40 weeks gestation; woman with chronic hypertension/gestational hypertension at least at 37 weeks gestation; woman with preeclampsia at least at 34 weeks gestation; woman with an uncomplicated dichorionic diamniotic (DCDA) twin pregnancy at least at 38 weeks gestation; woman with reduced fetal movements (RFM) at least at 37 weeks gestation; woman with signs of infection, bleeding or spontaneous rupture of membrane (SROM); woman with previous lower segment caesarean section at least at 40 weeks gestation; or woman with severe symphysis pubis dysfunction at least at 38 weeks gestation.

In one aspect, the method can include identifying a pregnant woman to be not suitable for induction of labor based on one or more criteria: woman with an uncomplicated pregnancy before 34 weeks gestation; woman of South Asian and Afro-Caribbean origin before 40 weeks gestation; woman that is at least 40 years old before 40 weeks gestation; woman with preterm prelabour rupture of membranes (PPROM) before 34 weeks gestation; woman with prelabour rupture of membranes (PROM) before 37 weeks gestation; woman with an estimated fetal weight (EFW) below 5th percentile before 37 weeks gestation but normal amniotic fluid and Doppler results; woman with fetal growth restriction (FGR) before 34 weeks gestation; woman with insulin-dependent diabetes mellitus (DM) before 38 weeks gestation; woman with gestational diabetes mellitus (GDM) before 40 weeks gestation; woman with chronic hypertension/gestational hypertension before 37 weeks gestation; woman with preeclampsia at least at 34 weeks gestation; woman with an uncomplicated dichorionic diamniotic (DCDA) twin pregnancy before 38 weeks gestation; woman with reduced fetal movements (RFM) before 37 weeks gestation; woman with signs of infection, bleeding or spontaneous rupture of membrane (SROM); woman with previous lower segment caesarean section before 40 weeks gestation; or woman with severe symphysis pubis dysfunction before 38 weeks gestation.

In one embodiment, a method of performing an induction of labor procedure on a pregnant woman can include: performing a method of determining suitability of a pregnant woman to be a candidate for induction of labor; and administering an agent that causes induction of labor in the woman. In one aspect, the method can include performing a subsequent method of determining suitability of pregnant woman for induction of labor in accordance with one of the methods of claims 1-27 after being administered the agent that causes induction of labor in the woman for a defined period of time. In one aspect, the defined period of time is at least 6 hours, or 12 hours, or 18 hours, or 24 hours, or 36 hours, or 48 hours.

In one embodiment, a method of determining effectiveness of an induction of labor procedure can include: obtaining a vaginal fluid sample from a pregnant woman that has received an agent that causes induction of labor in women; contacting the vaginal fluid sample with a PAMG-1 antibody that binds with a PAMG-1; and detecting whether the PAMG-1 antibody binds with PAMG-1 in the vaginal fluid sample to form a PAMG-1-antibody complex. When the PAMG-1 antibody complex forms, the induction of labor procedure is determined to be effective. When the PAMG-1 antibody complex does not form, the induction of labor procedure is determined to be effective. In one aspect, the method can include contacting the vaginal fluid sample with at least two PAMG-1-specific monoclonal antibodies, wherein at least one of the antibodies binds to PAMG-1 when present in the sample to form a PAMG-1/monoclonal antibody complex. In one aspect, the method can include detecting the presence of the PAMG-1/monoclonal antibody complex in the sample only when the concentration of PAMG-1 in the sample is at or exceeds a predefined detection threshold. In one aspect, the method can include detecting the presence of the PAMG-1/monoclonal antibody complex in the sample only when the concentration of PAMG-1 in the sample is at or exceeds a predefined detection threshold of 4 ng/ml. In one aspect, the method can include predicting that the pregnant woman will go into labor if PAMG-1 is detected in the vaginal sample, or predicting that the pregnant woman will not go into labor if PAMG-1 is not detected in the vaginal sample. In one aspect, the method can include recommending that the pregnant woman be examined to determine the reason there is no induction of labor if PAMG-1 is not detected in the vaginal sample, or recommending that the pregnant woman be prepared for labor if PAMG-1 is detected in the vaginal sample. In one aspect, the method can include providing information regarding caesarean section to the pregnant woman if PAMG-1 is not detected in the vaginal sample. In one aspect, the method can include determining whether fetal membranes of the pregnant woman are intact. If intact, the induction of labor procedure is determined to be not effective. If not intact, the induction of labor procedure is determined to be effective. In one aspect, the method can include collecting the vaginal fluid sample from the pregnant woman with a collection device, such as in accordance with the collection method and collection devices described herein. In one aspect, the induction of labor procedure is determined to be effective when PAMG-1 is determined to be present at or above the predefined detection threshold. In one aspect, the PAMG-1 is determined to be absent from the vaginal sample even if present at less than 4 ng/ml. In one aspect, the induction of labor procedure is determined to be ineffective when PAMG-1 is determined to be absent or below the predefined detection threshold.

In one embodiment, the pregnant woman prior to receiving the agent that causes induction of labor in women is selected to have one or more of the following criteria: woman with an uncomplicated pregnancy at least at term plus 7 days; woman of South Asian and Afro-Caribbean origin at least at 40 weeks gestation; woman that is at least 40 years old at least at 40 weeks gestation; woman with preterm prelabour rupture of membranes (PPROM) at least at 34 weeks gestation; woman with prelabour rupture of membranes (PROM) at least at 37 weeks gestation; woman with an estimated fetal weight (EFW) below 5th percentile after 37 weeks gestation but normal amniotic fluid and Doppler results; woman with fetal growth restriction (FGR) at least at 34 weeks gestation; woman with insulin-dependent diabetes mellitus (DM) at least at 38 weeks gestation; woman with gestational diabetes mellitus (GDM) at least at 40 weeks gestation; woman with chronic hypertension/gestational hypertension at least at 37 weeks gestation; woman with preeclampsia at least at 34 weeks gestation; woman with an uncomplicated dichorionic diamniotic (DCDA) twin pregnancy at least at 38 weeks gestation; woman with reduced fetal movements (RFM) at least at 37 weeks gestation; woman with signs of infection, bleeding or spontaneous rupture of membrane (SROM); woman with previous lower segment caesarean section at least at 40 weeks gestation; or woman with severe symphysis pubis dysfunction at least at 38 weeks gestation.

In one embodiment, a kit can include: a device for detecting placental alpha macroglobulin-1 (PAMG-1) in a vaginal fluid sample, the device being capable of detecting PAMG-1 at a level above a predetermined detection threshold; a vaginal swab; and instructions to use the kit. The kit can be used for determining suitability of a pregnant woman for induction of labor, wherein the instructions indicate the woman is not suitable for induction of labor when PAMG-1 is detected at or above the predetermined threshold, wherein the instructions indicate the woman is suitable for induction of labor when PAMG-1 is below the predetermined detection threshold. The kit can also be used for determining effectiveness of an induction of labor procedure, wherein the instructions indicate the induction of labor procedure was effective when PAMG-1 is detected at or above the predetermined threshold, wherein the instructions indicate the induction of labor procedure was ineffective when PAMG-1 is below the predetermined detection threshold. In one aspect, the vaginal swab is flocked. In one aspect, the kit can include a vial having a solution for receiving the PAMG-1 from the vaginal swab. In one aspect, the vaginal flocked swab has a conical shape that narrows toward the tip is adapted to collect vaginal fluid samples having PAMG-1. In one aspect, the vaginal flocked swab has a flattened conical shape that narrows toward the tip is adapted to collect vaginal fluid samples having PAMG-1, where it is more conical along a first profile and flatter along a second profile that is orthogonal with the first profile. In one aspect, the kit can include instructions for a protocol to obtain the vaginal fluid sample from the pregnant woman. In one aspect, the device has a predetermined detection threshold of 1 ng/ml for PAMG-1 in a sample. The predetermined detection threshold can be obtained by the dilution effect, which can be 4:1 or approximately 4:1, and which can provide for the predetermined detection threshold of 1, 2, 3, or 4 ng/ml depending on the sample and collection device along with the solvent solution (e.g., volume) that receives the PAMG-1 from the collection device. In one aspect, the predetermined detection threshold is 4 ng/ml for the combination of the device and vaginal swab, wherein the vaginal swab obtains the vaginal fluid sample and releases PAMG-1 into a solution that is applied to the device. In one aspect, the kit can include a solution, wherein the predetermined detection threshold is 4 ng/ml for the combination of the device, vaginal swab and solution, wherein the vaginal swab obtains the vaginal fluid sample and releases PAMG-1 into the solution that is applied to the device. In one aspect, the kit can include a first and a second monoclonal antibody specific for PAMG-1. In one aspect, the first and second PAMG-1-specific monoclonal antibodies have different binding specificities and affinities for PAMG-1.

In one embodiment, the device is a lateral flow device. In one aspect, the device comprises a pad region and a test region. In one aspect, the pad region of the test device comprises one of the first and second PAMG-1-specific monoclonal antibodies and the test region comprises the other of the first and second PAMG-1-specific monoclonal antibodies, and wherein the PAMG-1-specific monoclonal antibody in the pad region is mobilizable and the PAMG-1-specific monoclonal antibody in the test region is immobilized In one aspect, the mobilizable antibody in the pad region is M271, produced by hybridoma N271, deposited with the Russian National Collection of Industrial Microorganisms (VKPM) Depository and assigned accession number VKPM-93, and the immobilized antibody in the test region is M52, produced by hybridoma N52, deposited with the VKPM and assigned accession number VKPM-92. In one aspect, the test region of the test device further comprises a control region.

In one embodiment, the combination of the vaginal flocked swab and solution result in at least about 80% yield of PAMG-1 transfer from the vaginal flocked swab to the solution. In one aspect, the combination of the vaginal flocked swab and solution result in about 80-90% yield of PAMG-1 transfer from the vaginal flocked swab to the solution. In one aspect, the device is capable of detecting the presence of PAMG-1 in a sample when present at a level above 2 ng/ml. In one aspect, the device is capable of detecting the presence of PAMG-1 in a sample when present at a level above 3 ng/ml. In one aspect, the vaginal flocked swab is adapted to collect vaginal fluid samples having PAMG-1. In one aspect, the combination of the device and vaginal flocked swab results in a predefined detection threshold level of PAMG-1 being 4 ng/ml in the vaginal fluid.

In one embodiment, a method of determining suitability of a pregnant woman to be a candidate for induction of labor can include: obtaining a vaginal fluid sample from a pregnant woman; contacting the vaginal fluid sample with a PAMG-1 antibody that binds with PAMG-1; and detecting whether the PAMG-1 antibody binds with PAMG-1 in the vaginal fluid sample to form a PAMG-1-antibody complex, the detecting having a lower limit detection threshold of 1 ng/ml of PAMG-1. When the PAMG-1-antibody complex forms, the pregnant woman is determined to be in a condition that is not suitable for induction of labor because PAMG-1 is detected in the vaginal sample. When the PAMG-1-antibody complex does not form, the pregnant woman is determined to be in a condition that is suitable to be a candidate for induction of labor because the PAMG-1 is not detected in the vaginal sample. In one aspect, the method can include detecting the presence of the PAMG-1/monoclonal antibody complex only when the concentration of PAMG-1 in the vaginal sample is at or exceeds a predefined detection threshold of 1 ng/ml. In one aspect, a predefined detection threshold level of PAMG-1 is 1 ng/ml in the vaginal sample for detecting whether the PAMG-1 antibody binds with PAMG-1 to form the PAMG-1-antibody complex. In one aspect, PAMG-1 is determined to be present in the vaginal fluid at or above about 1 ng/ml. In one aspect, the pregnant woman is determined to be not suitable for induction of labor when PAMG-1 is determined to be present at or above the predefined detection threshold. In one aspect, PAMG-1 is determined to be absent from the vaginal sample even if present at less than 1 ng/ml. In one aspect, the pregnant woman is determined to be suitable for induction of labor when PAMG-1 is determined to be absent or below the predefined detection threshold.

In one embodiment, a method of determining effectiveness of an induction of labor procedure can include: obtaining a vaginal fluid sample from a pregnant woman that has received an agent that causes induction of labor in women; contacting the vaginal fluid sample with a PAMG-1 antibody that binds with a PAMG-1; and detecting whether the PAMG-1 antibody binds with PAMG-1 in the vaginal fluid sample to form a PAMG-1-antibody complex, the detecting having a lower limit detection threshold of 1 ng/ml of PAMG-1. When the PAMG-1 antibody complex forms, the induction of labor procedure is determined to be effective. When the PAMG-1 antibody complex does not form, the induction of labor procedure is determined to be ineffective. In one aspect, the method can include detecting the presence of the PAMG-1/monoclonal antibody complex in the sample only when the concentration of PAMG-1 in the sample is at or exceeds a predefined detection threshold of 1 ng/ml. In one aspect, the predefined detection threshold level of PAMG-1 is 1 ng/ml for detecting whether the PAMG-1 antibody binds with PAMG-1 in the vaginal fluid sample to form the PAMG-1-antibody complex. In one aspect, PAMG-1 is determined to be present in the vaginal fluid when present at or above about 4 ng/ml. In one aspect, the induction of labor procedure is determined to be effective when PAMG-1 is determined to be present at or above the predefined detection threshold. In one aspect, PAMG-1 is determined to be absent from the vaginal sample even if present at less than 1 ng/ml. In one aspect, the induction of labor procedure is determined to be ineffective when PAMG-1 is determined to be absent or below the predefined detection threshold.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

Figure 1:
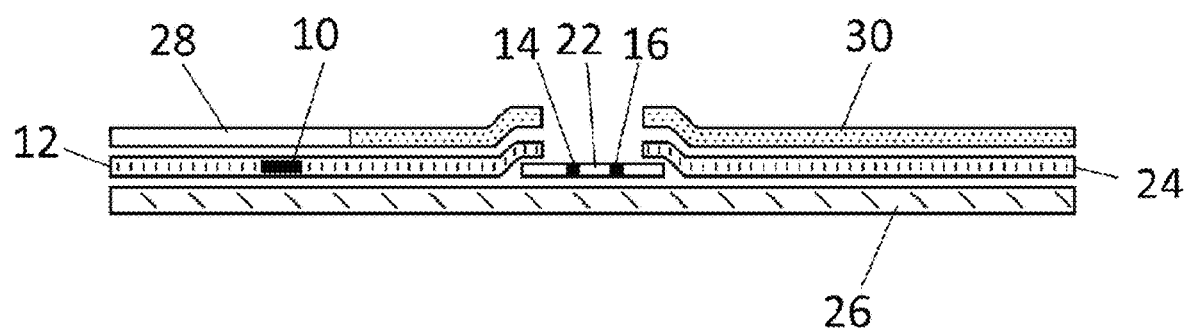
FIG. 1 is a schematic longitudinal sectional view.

The elements in the figures are arranged in accordance with at least one of the embodiments described herein, and which arrangement may be modified in accordance with the disclosure provided herein by one of ordinary skill in the art.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present technology relates to devices, kits and methods for the accurate determination of whether or not a pregnant woman is suitable for receiving an induction of labor procedure (IOLP). If the pregnant woman is suitable, then the IOLP can be performed, which can lead to labor and birth. If the pregnant woman is not suitable, then the IOLP should not be performed on the woman. However, in one aspect showing a sign of imminent labor may be an indication that the woman is not suitable for an IOLP because it is likely she will progress to labor naturally (e.g., without the induction of labor event).

Also, the present technology relates to devices, kits and methods for the accurate determination of whether or not an IOLP was effective. When effective, an IOLP can lead to labor and birth, preferably vaginal delivery without mechanical assistance (most preferred), or vaginal delivery with mechanical assistance (less preferred), or caesarean section (least preferred). Commonly the IOLP includes administration of oxytocin (e.g., Pitocin), where optionally prostaglandins may also be administered.

The devices, kits and methods can assess whether or not PAMG-1 is present before, during and/or after the IOLP.

The PAMG-1 can be assessed prior to an IOLP to determine if the pregnant woman is suitable to receive the IOLP. Vaginal fluid with PAMG-1 below a predetermined threshold indicates the pregnant woman is suitable to receive the IOLP. Vaginal fluid with PAMG-1 at or above a predetermined threshold indicates the pregnant woman is not suitable to receive the IOLP.

The PAMG-1 can be assessed after the IOLP to determine if the IOLP was effective. Vaginal fluid with PAMG-1 below a predetermined threshold indicates the IOLP was not effective. Vaginal fluid with PAMG-1 at or above a predetermined threshold indicates the IOLP was effective.

In some instances, the devices, kits, and methods can assess a change in amount of PAMG-1 when the amount of PAMG-1 is measured before and after the IOLP.

If PAMG-1 is detected prior to or during the IOLP, the amount detected after the IOLP is compared to the amount prior to or during the procedure. An increase in PAMG-1 can be indicative of a successful IOLP and indicate imminent delivery (e.g., within 24 hours, 12 hours, 6 hours, 3 hours, 2 hours, or 1 hour).

If PAMG-1 is not detected prior to or during the IOLP, the presence of PAMG-1 or the amount detected after the IOLP can be indicative of a successful IOLP and indicate imminent delivery (e.g., within 24 hours, 12 hours, 6 hours, 3 hours, 2 hours, or 1 hour).

If PAMG-1 is not detected after the IOLP, it can be determined that the IOLP was not effective.

In one scenario, when the amount of PAMG-1 before the IOLP is below the detection threshold for PAMG-1, and the amount of PAMG-1 detected after the IOLP is above the detection threshold for PAMG-1, the result is for a positive outcome of the IOLP (e.g., effective). This outcome indicates that labor and birth are imminent (e.g., imminent delivery).

In one scenario, when the amount of PAMG-1 before the IOLP is below the detection threshold for PAMG-1, and the amount of PAMG-1 detected after the IOLP is still below the detection threshold for PAMG-1, the result is for a negative outcome of the IOLP (e.g., ineffective). This outcome indicates that labor and birth are not imminent (e.g., no imminent delivery) even after performing the IOLP.

In one scenario, when the amount of PAMG-1 before the IOLP is above the detection threshold for PAMG-1 and the IOLP is still performed, and the amount of PAMG-1 detected after the IOLP is still above the detection threshold for PAMG-1, the result is for a neutral outcome of the IOLP. Here, the relative amounts in a quantitative assessment is performed before the IOLP compared to after the IOLP, and when before has higher PAMG-1 the result is negative (e.g., ineffective), when after has higher PAMG-1 the result is positive (e.g., effective). The effective result indicates that labor and birth are imminent (e.g., imminent delivery).

In one scenario, when the amount of PAMG-1 before the IOLP is above the detection threshold for PAMG-1, and the amount of PAMG-1 detected after the IOLP is then below the detection threshold for PAMG-1, the result is for a null outcome of the IOLP. This outcome indicates that the IOLP may not have been effective, but also may indicate that the PAMG-1 analysis was compromised. This result can result in a recommendation for a retest of the PAMG-1 by performing a completely new PAMG-1 analysis.

In one scenario, when the amount of PAMG-1 before the IOLP is above the detection threshold for PAMG-1, the IOLP is determined to not be necessary. Here, the IOLP can be omitted. If in some predetermined time after the test for PAMG-1 that was positive there has not been labor or delivery, the PAMG-1 may be analyzed again and optionally compared to the original analysis. If the second PAMG-1 analysis is negative or below the detection threshold, then the IOLP can then be performed. Subsequent to the IOLP, the PAMG-1 analysis can again be performed, where the results of the PAMG-1 analysis can be compared to the prior analyses (e.g., quantitative or qualitative).

In some instances, the PAMG-1 analysis can be a qualitative analysis with a positive reading for PAMG-1 above the detection threshold and a negative reading for PAMG-1 below the detection threshold.

In some instances, the PAMG-1 analysis can be a quantitative analysis where the amount detected above the detection threshold is compared to standard, control, or calibrated curve. Accordingly, an amount of PAMG-1 may be determined for the pregnant woman and recorded for comparison with amounts at other time points.

The PAMG-1 analysis before the IOLP can be used to screen for candidates for the procedure. When no PAMG-1 is detected (e.g., below detection threshold), then the pregnant woman may be a candidate (e.g., suitable) for the IOLP. When PAMG-1 is detected (e.g., above the detection threshold), then the pregnant woman may not be a candidate (e.g., not suitable) for the IOLP. However, if the amount detected PAMG-1 level is low (e.g., close to the detection threshold), then the pregnant woman may be a candidate (e.g., suitable) or the pregnant woman is a candidate for another PAMG-1 analysis protocol.

Accordingly, the PAMG-1 analysis can be used to (1) determine if a pregnant woman is a candidate for an IOLP (e.g., PAMG-1 below the threshold before IOLP); and (2) determine if the IOLP was effective (e.g., PAMG-1 is at above the threshold after IOLP).

Once the PAMG-1 indicates the IOLP was effective, then the pregnant woman can undergo further evaluations and diagnostics, such as those described herein for positive PAMG-1 results.

In one aspect, after it is determined that the IOLP was successful, then the patient may be analyzed for imminent delivery (e.g., within 24 hours, 12 hours, 6 hours, 3 hours, 2 hours, or 1 hour). This can include a time to delivery analysis.

In one aspect, a patient that has a positive PAMG-1 analysis with levels above the threshold may not be a candidate for induction of labor because they may be ready for imminent delivery (e.g., within 14 days, 7 days, 48 hours, 36 hours, 24 hours, 18 hours, 12 hours, 6 hours, 3, hours, 2 hours, or 1 hour etc.), particularly in patients presenting with signs, symptoms or complaints suggestive of labor.

In one embodiment, a method of determining whether a pregnant woman is a candidate for undergoing an IOLP can include analyzing PAMG-1. The analysis of PAMG-1 can include (a) contacting a vaginal fluid sample obtained from a pregnant woman with at least two PAMG-1-specific monoclonal antibodies, wherein at least one of the antibodies binds to PAMG-1 when present in the sample to form a PAMG-1/monoclonal antibody complex; (b) testing for the presence of the PAMG-1/monoclonal antibody complex in the sample that indicates the concentration of PAMG-1 in the sample exceeds a predefined detection threshold; (c) determining that PAMG-1 is in the sample above the predefined threshold; and (d) determining the pregnant woman is not a candidate for the IOLP because PAMG-1 was detected in the vaginal fluid.

In one embodiment, a method of determining whether a pregnant woman is a candidate for undergoing an IOLP can include analyzing PAMG-1. The analysis of PAMG-1 can include (a) contacting a vaginal fluid sample obtained from a pregnant woman with at least two PAMG-1-specific monoclonal antibodies, wherein at least one of the antibodies binds to PAMG-1 when present in the sample to form a PAMG-1/monoclonal antibody complex; (b) testing for the presence of the PAMG-1/monoclonal antibody complex in the sample that indicates the concentration of PAMG-1 in the sample exceeds a predefined detection threshold; (c) determining that PAMG-1 is not in the sample above the predefined threshold; and (d) determining the pregnant woman is a candidate for the IOLP because PAMG-1 was not detected.

In one embodiment, a secondary PAMG-1 analysis can be performed to confirm the results of a primary PAMG-1 analysis. When the secondary and primary PAMG-1 analyses contradict, other information may be employed to make the determination for suitability of candidacy for the IOLP. When the secondary and primary PAMG-1 analyses contradict, a third PAMG-1 analysis can be performed, and the two same results of the three PAMG-1 analysis are used for the determination.

In one embodiment, a method of determining whether an IOLP was successful (e.g., effective) to induce labor can include analyzing PAMG-1. The analysis of PAMG-1 can include: (a) obtaining a vaginal fluid sample obtained from a pregnant woman that has undergone an IOLP; (b) contacting the vaginal fluid sample obtained from a pregnant woman with at least two PAMG-1-specific monoclonal antibodies, wherein at least one of the antibodies binds to PAMG-1 when present in the sample to form a PAMG-1/ monoclonal antibody complex; (c) testing for the presence of the PAMG-1/monoclonal antibody complex in the sample that indicates the concentration of PAMG-1 in the sample exceeds a predefined detection threshold; (d) determining that PAMG-1 is in the sample above the predefined threshold; and (e) determining the IOLP was successful because PAMG-1 was detected. Subsequent to determining that the IOLP was successful, time to delivery or other analysis may be performed.

In one embodiment, a method of determining whether an IOLP was not successful (e.g., ineffective) to induce labor can include analyzing PAMG-1. The analysis of PAMG-1 can include: (a) obtaining a vaginal fluid sample obtained from a pregnant woman that has undergone an IOLP; (b) contacting the vaginal fluid sample obtained from a pregnant woman with at least two PAMG-1-specific monoclonal antibodies, wherein at least one of the antibodies binds to PAMG-1 when present in the sample to form a PAMG-1/monoclonal antibody complex; (c) testing for the presence of the PAMG-1/monoclonal antibody complex in the sample that indicates the concentration of PAMG-1 in the sample exceeds a predefined detection threshold; (d) determining that PAMG-1 is not in the sample above the predefined threshold; and (e) determining the IOLP was not successful because PAMG-1 was not detected. Subsequent to determining that the IOLP was not successful, a secondary IOLP may be performed or further analysis can be performed to determine the reason that the IOLP was not successful.

In one embodiment, the methods require analyzing PAMG-1 before and after an IOLP on a pregnant woman, such as when testing to determine if the woman is a candidate for the IOLP and then testing to determine if the IOLP was effective so as to cause labor to be induced. As such, the kit having a first device and flocked swab combination to be used before the IOLP, and a second device and flocked swab combination to be used after the IOLP.

In any of the procedures for analyzing PAMG-1, the predetermined detection threshold level of PAMG-1 in the vaginal fluid can be 4 ng/ml. That is, the vaginal fluid having 4 ng/ml of PAMG-1 can be detected with the kits described herein (e.g., device with swab). However, with the device having a detection threshold for PAMG-1 being as low as 1 ng/ml in a sample, the methods may be optimized to be capable of being performed with the predetermined detection threshold being lowered to 3 ng/ml, 2 ng/ml, or even 1 ng/ml.

In any of the procedures for analyzing PAMG-1, the at least two PAMG-1 specific monoclonal antibodies can be used in a lateral flow device. The lateral flow device can include a pad region and a test region. The pad region of the test device can include one of the at least two PAMG-1 specific monoclonal antibodies and the test region can include the other of the two. In certain aspects, the PAMG-1 specific monoclonal antibody in the pad region is mobilizable and the PAMG-1 specific monoclonal antibody in the test region is immobilized. In some aspects, the test region of the test device further includes a control region. In some aspects, each of the at least two PAMG-1-specific monoclonal antibodies is an antibody selected from the group consisting of M271, produced by hybridoma N271, deposited with the Russian National Collection of Industrial Microorganisms (VKPM) Depository and assigned accession number VKPM-93; M52, produced by hybridoma N52, deposited with the VKPM and assigned accession number VKPM-92; and M42, produced by hybridoma N42, deposited with the VKPM and assigned accession number VKPM-94.

In any of the procedures for analyzing PAMG-1, the mobilizable antibody in the pad region can be M271, produced by hybridoma N271, deposited with the Russian National Collection of Industrial Microorganisms (VKPM) Depository and assigned accession number VKPM-93, and the immobilized antibody in the test region can be M52, produced by hybridoma N52, deposited with the VKPM and assigned accession number VKPM-92.

Figure 2:
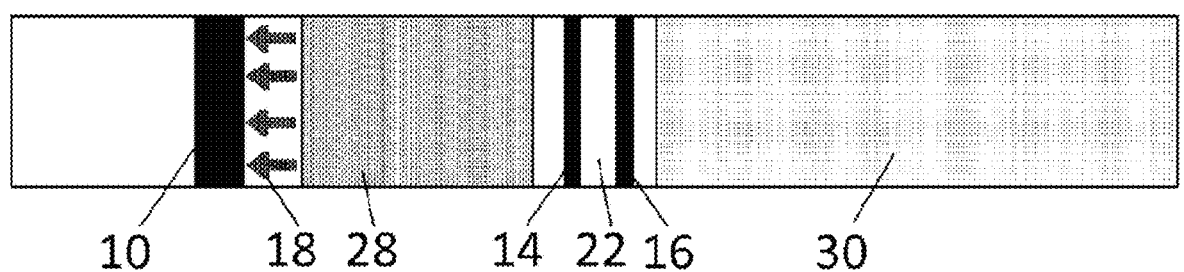
FIG. 2 is a planar view of an exemplary device that can be used to detect the presence of PAMG-1 in a vaginal fluid sample (e.g., for diagnosing time to delivery (TTD)). The numbers identify the following components of the exemplary device: 10—M271 antibody region; 12—pad; 14—test region; 16—control region; 18—arrows; 22—nitrocellulose membrane; 24—filter paper membrane; 26—adhesive rigid plastic base; 28—partially transparent protective film with arrows; and 30—non-transparent protective film.

In any of the procedures for analyzing PAMG-1, the device can be the device illustrated in FIGS. 1 and 2.

In certain aspects, the present disclosure provides a kit for determining whether a pregnant woman is a candidate for undergoing an IOLP, which can include a device for analyzing PAMG-1.

In certain aspects, the present disclosure provides a kit for determining whether an IOLP was successful to induce labor, which can include a device for analyzing PAMG-1.

In any of the kits, the device can be any device for detecting the presence of PAMG-1 in a vaginal fluid sample when present at a level above a predetermined threshold. The kits can also include a vaginal swab. In some aspects, the vaginal swab can be flocked. In some aspects, the kit further includes a vial having a solution for withdrawing PAMG-1 from the vaginal swab and for placement on the device, which can be referred to as a transfer solution. In some instances, the kit can further include instructions for use in one or more of the methods described herein, such as method steps for determining whether a pregnant woman is a candidate for undergoing an IOLP, and/or method steps for determining whether an IOLP was successful to induce labor. In certain aspects, the predetermined threshold is 4 ng/ml of PAMG-1 in the vaginal fluid. In yet other aspects, the device includes a first and a second monoclonal antibody specific for PAMG-1. The first and second PAMG-1-specific monoclonal antibodies can have different binding specificities and affinities for PAMG-1. In some aspects, each of the first and second PAMG-1-specific monoclonal antibodies can be an antibody selected from the group consisting of M271, produced by hybridoma N271, deposited with the Russian National Collection of Industrial Microorganisms (VKPM) Depository and assigned accession number VKPM-93; M52, produced by hybridoma N52, deposited with the VKPM and assigned accession number VKPM-92; and M42, produced by hybridoma N42, deposited with the VKPM and assigned accession number VKPM-94. In yet other aspects, the test device is a lateral flow device. The test device can include a pad region and a test region. The pad region of the test device can include one of the first and second PAMG-1-specific monoclonal antibodies and the test region can include the other of the first and second PAMG-1-specific monoclonal antibodies. In certain aspects, either or both of the pad and test regions can contain additional PAMG-1-specific monoclonal antibodies and/or mixtures of the first two PAMG-1-specific monoclonal antibodies. In certain aspects, the PAMG-1-specific monoclonal antibody in the pad region can be mobilizable and the PAMG-1-specific monoclonal antibody in the test region can be immobilized. In still other aspects, the mobilizable antibody in the pad region is M271, produced by hybridoma N271, deposited with the Russian National Collection of Industrial Microorganisms (VKPM) Depository and assigned accession number VKPM-93, and the immobilized antibody in the test region is M52, produced by hybridoma N52, deposited with the VKPM and assigned accession number VKPM-92. In some aspects, the test region of the test device further includes a control region. In some aspects, the device in the kit is the device illustrated in FIGS. 1 and 2.

FIG. 1 is a schematic longitudinal sectional view and FIG. 2 is a planar view of an exemplary device that can be used to detect the presence of PAMG-1 in a vaginal fluid sample. The numbers identify the following components of the exemplary device: 10—M271 antibody region; 12—pad; 14—test region; 16—control region; 18—arrows; 22—nitrocellulose membrane; 24—filter paper membrane; 26—adhesive rigid plastic base; 28—partially transparent protective film with arrows; and 30—non-transparent protective film.

In general, the methods disclosed herein include detecting the presence of PAMG-1 when present in the vaginal fluid at a level above a predefined detection threshold.

Subsequent to the procedure for determining whether a pregnant woman is a candidate for an IOLP, if the PAMG-1 is detected, the presently disclosed methods can predict TTD and/or rule out spontaneous preterm delivery with a high PPV and a high NPV. A positive test showing PAMG-1 prior to performing an induction of labor protocol, can indicate that delivery is imminent (e.g., within 14 days, 7 days, 48 hours, 36 hours, 24 hours, 18 hours, 12 hours, 6 hours, 3, hours, 2 hours, 1 hour, etc.). A negative test (absence of detection of PAMG-1) indicates that delivery is not likely to occur within 14 days, 7 days, or 48 hours, and thereby the pregnant woman is a candidate for an IOLP. A positive test (PAMG-1 is detected) before performing an IOLP can also indicate that a pregnant woman is at risk of spontaneous preterm premature ROM and/or preterm delivery, and thereby it is determined that the pregnant woman is not a candidate for an IOLP. On the other hand, a negative test (absence of detection of PAMG-1) indicates that a pregnant woman is not at risk of spontaneous preterm premature ROM or preterm delivery, and thereby the woman is a candidate for an IOLP.

The PAMG-1 is a protein found in high concentrations in amniotic fluid but very low concentrations in background levels of cervico-vaginal discharge. In recent years, the medical community has increasingly accepted the widespread use of detecting PAMG-1 to aid the provider in confirming or ruling out rupture of fetal membranes (ROM). The test used is commercially marketed as the AmniSure® ROM Test, manufactured by AmniSure® International, LLC, Boston, Mass., USA. In a previous investigation of the utility of PAMG-1 for the detection of ROM, it was noted that in 20 out of the 23 cases where the AmniSure® ROM Test was positive and standard clinical assessment (i.e., nitrazine, ferning and pooling) was negative, the patient was ultimately determined to have been ruptured upon retrospective analysis of her clinical course (see, Lee S E, et al. Obstet Gynecol 2007; 109:634-640). It was later reported that for all of the preterm patients in the group that showed signs and symptoms of labor, delivery followed within 7 days (see, Lee S M, et al. J Matern Fetal Neonatal Med 2009; 22:305-310). The clinical value of a positive AmniSure® ROM Test in the patient presenting with signs and symptoms of preterm labor (PTL) but without ROM was also investigated. The results demonstrated that the AmniSure® ROM Test was predictive of delivery of these patients within 48 hours, 7 days and 14 days (see, Lee M S, et al. J Matern Fetal Neonatal Med. 2012 September; 25(9):1690-8). Now, however, the test can be applied to determine whether a woman is a candidate for an IOLP, and/or to determine whether an IOLP was successful.

While not intending to be bound by any one particular theory or mechanism of action, the present methods are believed to provide superior performance such as, e.g., PPV and NPV, as well as sensitivity (SN) and specificity (SP), at least in part, by providing a diagnostic test that has an increased sensitivity for detecting PAMG-1 in vaginal secretion samples compared to certain currently available diagnostic methods. For example, while currently available tests that detect PAMG-1 utilize a detection threshold of 5 ng/ml of PAMG-1 in vaginal fluid, it has been discovered that optimization of the devices and/or methods can be used for adjusting the detection threshold to down 4 ng/ml of PAMG-1 in vaginal fluid, which provides a surprisingly improved diagnostic test (e.g., high PPV and high NPV). It was unexpected that the 4 ng/ml detection threshold could be used in a method for determining whether a woman is a candidate for an IOLP, and/or to determine whether an IOLP was successful. Based on the data for testing PAMG-1 it is expected that the methods can be performed with a high PPV, as presently disclosed. In one aspect, the high PPV is unexpected because it was expected that decreasing the detection threshold below 5 ng/ml would increase the frequency of false positive results, thereby decreasing the PPV of the test, thus decreasing to 4 ng/ml is surprising and unexpected. Moreover, it was not previously realized that detecting concentrations of PAMG-1 below 5 ng/ml could be useful for determining whether a woman is a candidate for an IOLP, and/or to determine whether an IOLP was successful. Now, small concentrations of PAMG-1 (e.g., 4 ng/ml) in the vaginal fluid that were once thought to be of little clinical significance can be used for patient selection for determining whether a woman is a candidate for an IOLP, and/or to determine whether an IOLP was successful.

It is also presently discovered that the ideal gestational age of a pregnant woman suitable for determining whether she is a candidate for an IOLP, and/or to determine whether an IOLP was successful according to the methods disclosed herein is specifically later than 34 weeks or later than 36 weeks or later than 36 weeks, 6 days. Also, in certain embodiments, the tests disclosed herein are performed on a patient population having cervical dilatation of 3 cm or less.

In certain embodiments, a pregnant woman is suitable for and/or selected for determining whether she is a candidate for an IOLP if she has a gestational age later than 34 weeks or 36 weeks or 36 weeks, 6 days. In certain embodiments, a pregnant woman is suitable for and/or selected for determining whether she is a candidate for an IOLP, and/or determining whether an IOLP was successful, if she has a cervical length of 25 mm or more and/or cervical dilatation of 3 cm or less.

In diagnostic testing, the PPV, or precision rate, is the proportion of positive test results that are true positives (such as correct diagnoses of having PAMG-1 at or above 4 ng/ml in vaginal fluid). It is a critical measure of the performance of a diagnostic method, as it reflects the probability that a positive test reflects the underlying condition that is being tested for. Other important measures include negative predictive value (NPV), sensitivity (SN), and specificity (SP). NPV indicates the proportion of subjects with a negative test result who are correctly identified as not having the condition being tested (e.g., not having PAMG-1 at or above 4 ng/ml in vaginal fluid). A high NPV for a given test indicates that when the test yields a negative result, it is most likely correct in its assessment, and produces only rarely a false negative result. Thus, for predicting suitability of IOLP or determining whether the IOLP was effective (e.g., within a specific time frame), a high NPV means that the test only rarely predicts that they were not suitable or the procedure was not effective, in reality, they were indeed suitable or the test was effective. The number of true positive results and true negative results that a diagnostic test yields (e.g., in a clinical study), can also be combined to determine the sensitivity (SN) and specificity (SP) of a diagnostic test.

Here, it is expected to have a high PPV and a high NPV based on the surprising and unexpected benefits when reducing the detection threshold of PAMG-1 in vaginal fluid to 4 ng/ml.

As such, the IOLP is performed by: identifying a patient suitable for the IOLP; and administering the labor inducing drug (e.g., oxytocin or others). The performance of the IOLP may include other procedures, such as physical checkups, body fluid profile examination, gestation determination, predicting time of delivery or incapability of such prediction, or other protocol to determine if the pregnant woman is a candidate for IOLP. Also, the IOLP may include examinations subsequent to the administration of the labor inducing drug, such as testing for PAMG-1 or other biomarkers, examination of the cervix or other examinations.

In one embodiment, the method of determining effectiveness of IOLP is performed within 1 hour of performing the IOLP, or 1 hour and 15 minutes, or within 1 hour and 30 minutes, or within 1 hour and 45 minutes, or within 2 hours of the IOLP. However, the timeframe may vary Initiation of this method can include sampling the vaginal fluid and the steps for determining the presence of or otherwise analyzing PAMG-1. In one embodiment, the method can include waiting until the pregnant woman wants or needs to have the vaginal fluid sampled. The pregnant woman may want until certain pains, nausea or other uncomfortableness has reduced or subsided, or want to wait until feeling the onset of labor, such as contractions. The indications for the need to have the vaginal fluid sampled may include: too long of a period without any onset of labor (e.g., 1 hour after performing the IOLP, or after 2 hours, or after 3 hours, or after 4 hours of the IOLP), no contractions, no movement of fetus, lack of proper positioning of fetus for delivery, or others.

The methods disclosed herein may also include a patient that is selected for testing for IOLP if the patient presents with one or more of the following signs: (i) a gestational age later than 36 weeks, 6 days; and/or (ii) a cervical length of 25 mm or more; and/or (iii) a cervical dilatation of 3 cm or less. The methods disclosed herein are also useful for determining a pregnant woman's risks or countermeasures to inhibit risks, such as: administrating corticosteroids to improve respiratory development of the fetus, administration of antibiotics to decrease the risk of infection (intrapartum and post-partum), prescription of bed rest, and/or increased observation and fetal monitoring) can be taken, if necessary.

PAMG-1 was isolated in 1977 from amniotic fluid by D. Petrunin and was originally referred to as specific alpha-1 globulin of placenta (D. Petrunin, et al., "Immunological Identification of Organ Specific alpha-1 Globulin of Human Placenta and Its Content in the Amniotic Fluid," in Akusherstvo i Ginekologiya, 1977, N 1, pp. 64-65, Moscow, USSR).

The exemplary steps of the isolation of PAMG-1 from amniotic fluid of pregnant women are outlined in Table 1, and discussed, below. It is to be understood, however, that PAMG-1 can be isolated according to any suitable method known in the art, from any suitable source.

TABLE 1

Exemplary Steps of Isolation of PAMG-1

| Steps of Isolation | Purity (%) | Yield (%) |
|---|---|---|
| Amniotic fluid 16-25 weeks pregnancy | 4 | 100 |
| Precipitation by 0.5% lanthanum chloride | 25 | 90 |
| Precipitation by ammonium sulphate at 50% saturation | 35 | 70 |
| Precipitation by lithium sulphate at 60% saturation | 60 | 60 |
| Reverse Phase Chromatography Separation | 90 | 30 |

The PAMG-1 can be isolated from the amniotic fluid of pregnant women for any of the methods described herein. A 10% solution of lanthanum chloride can be added at the volumetric ratio 20:1 (so that its final concentration can be 0.5%) to the amniotic fluid and kept at 4° C. for 18 hours. The precipitate can be further separated by centrifugation at 8,000 rpm for 30 minutes. The precipitate can be dissolved in a saturated solution of $Na_2HPO_4$ and then the precipitate of insoluble lanthanum salts (produced in the process of centrifugation at 8,000 rpm for 30 minutes) can be separated. The resulting solution can be fractionated with 50% saturated ammonium sulphate by incubating at 4° C. for 18 hours, and the resulting precipitate can be dissolved in distilled water in such a way as to restore the volume of the dissolved precipitation fractions to the initial volume of the amniotic fluid. Then, the solution can be precipitated by 60% saturated lithium sulphate, and the precipitate can be dissolved in a small amount of distilled water. After dialysis, the admixtures were adsorbed with calcium pyrophosphate by adding an equal volume of moisture absorbent to the protein solution, intermixing and incubating for 10-15 minutes, and separating the absorbent by centrifugation. However, it can be preferable in the present methods to analyze PAMG-1 in vaginal fluid rather than amniotic fluid.

The molecular weight of PAMG-1 was first reported as 32 kDa (Boltovskaya, M. N. et al., "Histochemical and Clinico-Diagnostic Study of the Placental Alpha-Microglobulin [PAMG-1] Using Monoclonal Antibodies," in Bulletin of Experimental. Biology and Medicine, 1991, No. 10, pp. 397-400); however, it is generally accepted now that PAMG-1 has a molecular weight of 34 kDa (see, e.g., Pollet-Villard et al. (Amer J Perinatol 2011 June; 28(6):489-94)). PAMG-1 is a protein that is present in the serum, amniotic fluid and vaginal secretion of pregnant women. PAMG-1 exists in amniotic fluid at a concentration about at least 100 times greater than in the serum of pregnant women and at least 3000 times greater than in vaginal secretions of pregnant women in the absence of fetal membranes rupture. As a result, even when a small amount of amniotic liquid (about ¹/₁₀₀ of one drop per 1 ml of vaginal secretion) is dissolved in a vaginal secretion sample, a sufficient amount of PAMG-1 is present in this vaginal secretion sample to indicate that fetal membrane rupture has taken place or that labor is imminent. Further, because of the low concentration of PAMG-1 in blood serum, the insignificant admixture of blood serum to the vaginal fluid sample (10-15%) does not affect the results produced by the devices and methods of the present disclosure. Detection of PAMG-1 for the diagnosis of ROM has been shown to be superior to the detection of other amniotic proteins such as, e.g., IGFBP-1, a 28 kDa protein (see, Pollet-Villard et al. (supra) and European Guidelines on preterm labor (The Journal of Maternal-Fetal and Neonatal Medicine, 2011; Early Online, 1-9)).

Because the presence of amniotic fluid in a vaginal secretion can be indicative of a fetal membrane rupture or imminent labor, the detection of the amniotic protein PAMG-1 in vaginal secretion can be used for determining whether a pregnant woman is a candidate for an IOLP, and/or determining whether an IOLP was successful. However, it is presently discovered that the methods disclosed herein can be used to detect PAMG-1 in vaginal secretions even in the absence of detectable ROM to accurately determine if the IOLP was successful. The methods can be achieved with the detection threshold of PAMG-1 being about 4 ng/ml in vaginal fluid (e.g., using device and swab). While not intending to be bound by theory or limited to any one particular mechanism of action, it is believed that PAMG-1 is transudated through chorioamniotic pores in fetal membranes during uterine contractions that occur when delivery is imminent (i.e., will occur within, e.g., 14 days, 7 days, or 48 hours). Degradation of extracellular matrix of fetal membranes due to inflammatory process of labor and or infection may also lead to the finding of increased levels of PAMG-1 in cervico-vaginal secretions.

The methods disclosed herein encompass detecting the presence of PAMG-1 protein in vaginal secretion samples obtained from pregnant women. PAMG-1 protein can be detected according to any suitable method known in the art.

An exemplary method for the detection of PAMG-1 in vaginal fluid samples includes, but is not limited to, immunoassay (e.g., ELISA), using, e.g., PAMG-1 specific antibodies (e.g., monoclonal antibodies or antigen-binding fragments thereof) described herein.

PAMG-1 antibodies, as disclosed herein, can detect very low concentrations of PAMG-1. For example, concentration of 1 ng/ml PAMG-1 can be detected with the device. Because the maximum concentration of PAMG-1 in serum is about 25 ng/ml, as compared to a minimum concentration of about 1680 ng/ml in amniotic fluid, and because the background concentration of PAMG-1 in vaginal secretions is very low, about 0.2 ng/ml, a lower threshold level for PAMG-1 can be used in the methods of the present disclosure for detecting the occurrence of amniotic fluid in the vagina. It is presently discovered that a predefined threshold of about 4 ng/ml for PAMG-1 in vaginal fluid can be used in the methods disclosed herein when the device and flocked vaginal swab are used.

As a result, the devices and methods of the present disclosure are not influenced by the presence of vaginitis or other variables, which had a negative impact on the accuracy of prior methods for assaying PAMG-1. The maximum concentration of PAMG-1 in inflammation exudate is 3 ng/ml (see, e.g., U.S. Pat. No. 7,709,272 by Fuks et al.). The same concentration of PAMG-1 may occur if blood serum admixture to vaginal secretion does not exceed 10-15%. In addition, a large ratio of concentrations serum-to-amniotic PAMG-1 makes the devices and methods of the present disclosure significantly less likely to produce false positive results due to the presence of blood serum in vaginal secretions, even with a low PAMG-1-detection threshold.

The present disclosure provides methods and devices and systems for predicting suitability for IOLP and/or determining effectiveness of IOLP at a PAMG-1 detection threshold of about 4 ng/ml in vaginal fluid.

PAMG-1 polypeptide separated from body fluids, produced recombinantly, or by chemical synthesis, and fragments or other derivatives or analogs thereof, including fusion proteins, may be used as an immunogen to generate antibodies that recognize the PAMG-1 polypeptide. The antibodies disclosed herein can include an immunoglobulin heavy chain of any isotype (e.g., IgG, IgE, IgM, IgD, IgA, and IgY), class (e.g., IgG1, IgG2, IgG3, IgG4, IgA1 and IgA2) or subclass of immunoglobulin molecules. PAMG-1 antibodies may have both a heavy and a light chain. Antibodies (including full length antibodies), monoclonal antibodies (including full length monoclonal antibodies), polyclonal antibodies, multispecific antibodies (e.g., bispecific antibodies), human, humanized or chimeric antibodies, and antibody fragments, e.g., Fab fragments, F(ab') fragments, fragments produced by a Fab expression library, epitope-binding fragments of any of the above, and engineered forms of antibodies, e.g., scFv molecules, so long as they exhibit the desired activity, e.g., binding to PAMG-1, can be used to perform the methods disclosed herein. Anti-PAMG-1 antibodies as, e.g., disclosed herein, may recognize PAMG-1 from one or more different mammalian species. Alternatively, an antibody disclosed herein may be specific for a single form of PAMG-1. In certain embodiments, an anti-PAMG-1 antibody is specific for human PAMG-1. PAMG-1 antibodies or antibody fragments or epitopes that bind with PAMG-1 can be prepared as known or developed or as disclosed in the incorporated references.

Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include, for example, X-ray crystallography and 2-dimensional nuclear magnetic resonance. See, e.g., Epitope Mapping Protocols in Methods in Molecular Biology, Vol. 66, G. E. Morris, Ed. (1996.

Antibodies that recognize the same or overlapping epitopes can be identified in a simple immunoassay showing the ability of one antibody to block the binding of another antibody to a target antigen, i.e., a competitive binding assay. Competitive binding is determined in an assay in which the binding molecule being tested inhibits specific binding of a reference binding molecule to a common antigen, such as PAMG-1. Numerous types of competitive binding assays are known, for example: solid phase direct or indirect radioimmunoassay (RIA); solid phase direct or indirect enzyme immunoassay (EIA) sandwich competition assay (see Stahli et al., Methods in Enzymology 9:242 (1983)); solid phase direct biotin-avidin EIA (see Kirkland et al., J. Immunol. 137:3614 (1986)); solid phase direct labeled assay, solid phase direct labeled sandwich assay (see Harlow and Lane, Antibodies: A Laboratory Manual, Cold Spring Harbor Press (1988)); solid phase direct label RIA using I-125 label (see Morel et al., Mol. Immunol. 25(1):7 (1988)); solid phase direct biotin-avidin EIA (Cheung et al., Virology 176:546 (1990)); and direct labeled RIA. (Moldenhauer et al., Scand. J. Immunol. 32:77 (1990)).

Typically, such an assay involves the use of purified antigen bound to a solid surface or cells bearing either of these, an unlabeled test binding molecule and a labeled reference binding molecule. Competitive inhibition is measured by determining the amount of label bound to the solid surface or cells in the presence of the test binding molecule. Usually the test binding molecule is present in excess. Usually, when a competing binding molecule is present in excess, it will inhibit specific binding of a reference binding molecule to a common antigen by at least 50-55%, 55-60%, 60-65%, 65-70% 70-75% or more.

Various procedures known in the art may be used for the production of polyclonal antibodies to PAMG-1 polypeptide or derivative or analog thereof. For the production of an antibody, various host animals can be immunized by injection with the PAMG-1 polypeptide, or a derivative (e.g., fragment or fusion protein) thereof, including but not limited to rabbits, mice, rats, sheep, goats, etc. In one embodiment, the PAMG-1 polypeptide or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the PAMG-1 polypeptide, or fragment, analog, or derivative thereof, any technique that provides for the production of antibody molecules by continuous cell lines in culture may be used. These include but are not limited to the hybridoma technique originally developed by Kohler and Milstein (Nature 1975, 256:495-497), as well as the trioma technique, the human B-cell hybridoma technique (Kozbor et al., Immunology Today 1983, 4:72; Cote et al., Proc. Natl. Acad. Sci. U.S.A. 1983, 80:2026-2030), and the EBV-hybridoma technique to produce human monoclonal antibodies (Cole et al., in Monoclonal Antibodies and Cancer Therapy, Alan R. Liss, Inc., pp. 77-96, 1985). In an additional embodiment of the present disclosure, monoclonal antibodies can be produced in germ-free animals (International Patent Publication No. WO 89/12690, published 28 Dec. 1989). In fact, according to the present disclosure, techniques developed for the production of "chimeric antibodies" (Morrison et al., J. Bacteriol. 1984, 159:870; Neuberger et al., Nature 1984, 312:604-608; Takeda et al., 1985, Nature 314:452-454) by splicing the genes from a mouse antibody molecule specific for a PAMG-1 polypeptide together with genes from a human antibody molecule of appropriate biological activity can be used; such antibodies are within the scope of this present disclosure. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the present disclosure, techniques described for the production of single chain antibodies (U.S. Pat. Nos. 5,476,786 and 5,132,405 to Huston; U.S. Pat. No. 4,946,778) can be adapted to produce PAMG-1 polypeptide-specific single chain antibodies. Indeed, these genes can be delivered for expression in vivo. An additional embodiment of the disclosure utilizes the techniques described for the construction of Fab expression libraries (Huse et al., Science 1989, 246:1275-1281) to allow rapid and easy identification of monoclonal Fab fragments with the desired specificity for a PAMG-1 polypeptide, or its derivatives, or analogs.

Antibody fragments that contain the idiotype of the antibody molecule can be generated by known techniques. For example, such fragments include but are not limited to: the F(ab)2 fragment which can be produced by pepsin digestion of the antibody molecule; the Fab fragments which can be generated by reducing the disulfide bridges of the F(ab)2 fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), Western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present disclosure. For example, to select antibodies which recognize a specific epitope of a PAMG-1 polypeptide, one may assay generated hybridomas for a product which binds to a PAMG-1 polypeptide fragment containing such epitope. For selection of an antibody specific to a PAMG-1 polypeptide from a particular species of animal, one can select on the basis of positive binding with PAMG-1 polypeptide expressed by or isolated from cells of that species of animal.

In certain aspects disclosed herein, the PAMG-1-specific monoclonal antibodies disclosed herein can be, e.g., M271, produced by hybridoma N271, deposited with the Russian National Collection of Industrial Microorganisms (VKPM) Depository and assigned accession number VKPM-93; M52, produced by hybridoma N52, deposited with the VKPM and assigned accession number VKPM-92; and M42, produced by hybridoma N42, deposited with the VKPM and assigned accession number VKPM-94. The binding properties and other characteristics of those PAMG-1 specific monoclonal antibodies are disclosed in detail in U.S. Pat. No. 7,709,272 to Fuks et al. Hybridoma cell lines producing, e.g., PAMG-1 specific antibodies, such as those disclosed above, can be produced by the following procedure. First, mice having spleen and lymph node B-cells are immunized with PAMG-1. Hybridomas are then produced to immortalize the B-cells. The B-cells may be spleen and/or lymph node B-cells. Those hybridomas, which produce a monoclonal antibody having a binding affinity for PAMG-1, are then identified in an ELISA: first layer: PAMG-1; second layer: hybridoma supernatant; and third layer: conjugate of rabbit anti-mouse antibodies labeled by horse radish peroxidase. These identified hybridomas are then cultivated in vitro or in ascites and the monoclonal antibodies they produce are isolated.

As disclosed herein, two or more PAMG-1 specific antibodies (e.g., monoclonal antibodies) can be used in combination to detect PAMG-1 in a vaginal fluid sample. In certain embodiments, at least one of the antibodies used in a method disclosed herein is detectably labeled. A variety of detectable markers can be used, including, but not limited to, stained particles, enzymes, fluorescent dyes, and radioactive isotopes. One particular example of a detectable marker is a gold stained particle having an average dimension in the range of 20 to 30 nm. Another example of a detectable marker is horseradish peroxidase. Methods for attaching a detectable marker to an antibody are described, for example, in Methods In Enzymology, 1981, Vol. 73, pp. 3-46 by Harlow, E., and Lane, D.; in "Antibodies a Laboratory Manual," Cold Spring Harbor Laboratory, 1988, pp. 322, 323, and 343; and Pierce Catalog, pp. T9-T17 (1996). Suitable enzymes include, but are not limited to, alkaline phosphatase and horseradish peroxidase. Other markers or labels for use according to the present disclosure include colloidal gold, colored latex beads, magnetic beads, fluorescent labels (e.g., fluorescene isothiocyanate (FITC), phycoerythrin (PE), Texas red (TR), rhodamine, free or chelated lanthanide series salts, especially Eu3+, to name a few fluorophores), chemiluminescent molecules, radio-isotopes (125I, 32P, 35S, chelated Tc, etc.) or magnetic resonance imaging labels. Other markers include fluorescence quenching and fluorescence transfer markers, e.g., as used in homogenous as well as solid phase assays. Furthermore, in accordance with the present disclosure a marker can be an epitope, binding partner, or "handle" for interaction with another molecule, such as biotin-streptavidin; glutathione-GST; hexahistidine-nickel; etc. The present disclosure also contemplates using secondary antibodies, which are themselves detectably labeled, as markers (e.g., in a situation where the anti-PAMG-1 antibody pair uses antibodies with Fc portions from two different animal species).

The antibodies disclosed herein can be mobilizable (e.g., able to move upon introduction of a fluid sample (e.g., in a flow device) and/or immobilized (e.g., in the test region of a strip device). Methods for immobilizing antibodies are well known in the art.

Immunoassays, particularly immunochromatographic assays, constitute a preferred technique in accordance with the present disclosure, and immunoassays are set forth in detail below. These assays have the advantage of specificity, accuracy, speed, and economy. Other methods for detecting and quantitating PAMG-1, however, can also be used. One such technique is mass spectrometry, e.g., using matrix-assisted laser-desorption (MALDI) time-of-flight (TOF) mass spectrometry (MS) with delayed extraction and a reflectron in the time-of-flight chamber. Preferably MALDI assays are performed on silicon arrays. An example of an array for MALDI is 200 µm circular gel pads at 350 µm centers, on oxidized silicon. A hydrophobic surface (repellent surface) between gelpads further provides a more focused matrix/protein spot for MALDI, thereby improving signal for quantitation. For example, spots produced using the Packard Bioscience system can be less than 200 µm in diameter. The Piezo system can deliver about 300 pL of MALDI matrix (e.g., DHB, sinapinic acid) to the exact position of the affinity capture agent-peptide spot to create a homogeneous peptide/matrix crystal. Desorption/Ionization (Karas, et al. Ion Processes, 1987, v. 78, pp. 53-68 or Zenobi, et al. Mass Spectrom. Rev. 1998, v. 17, pp. 337-366) from this crystal in a MALDI-MS (e.g., Perseptive Voyager) yields a mass spectrum where the height of a peptide peak is relative to the amount protein containing that peptide.

An alternative technique for use in the methods disclosed herein is capillary electrophoresis chromatography, which can permit quantitation of an analyte present in a small amount of sample.

Furthermore, quantitative biochemical techniques, such as polyacrylamide gel electrophoresis, high performance liquid chromatography, and the like may be employed, alone or in combination, to detect and quantitate the amount of PAMG-1 in a sample.

Such immunoassays using exemplary PAMG-1 specific antibodies encompassed by the presently disclosed methods are described in detail in U.S. Pat. No. 7,709,272 by Fuks et al.

Immunological Methods and Devices for Detecting PAMG-1

Various means known in the art for detecting immuno-specific binding of an antibody to an antigen can be used to detect the binding in accordance with the present disclosure.

An early method of detecting interaction between an antigen and an antibody involved in analysis of the complex is by precipitation in gels. A further method of detecting an analyte-detector antibody binding pair includes the use of radioiodinated detector antibodies or a radioiodinated protein which is reactive with IgG, such as Protein A. These early methods are well known to persons skilled in the art, as reviewed in Methods in Enzymology, 1980, v. 70, pp. 166-198.

Later methods for determining the presence of an analyte in a sample using only one antibody included competitive binding assays. In this technique the antibody, which most often would be immobilized onto a solid support, would be exposed to a sample suspected of containing the analyte together with a known quantity of labeled analyte. The two analytes, the labeled analyte and the analyte in the sample would then compete for binding sites on the antibody. Either free labeled analyte or bound labeled analyte is determined, and from this measurement the amount of competing analyte in the sample is known. A more complete description of this method is disclosed in "Basic Principles of Antigen-Antibody Reaction", Elvin A. Labat, (Methods in Enzymology, 70, 3-70, 1980). In this example the labeled analyte can be labeled with either a radioisotope or an enzyme label.

More current immunoassays utilize a double antibody method for detecting the presence of an analyte. These techniques are also reviewed in the above referenced volume of Methods in Enzymology. Therefore, according to one embodiment of the present disclosure, the presence of the individual markers is determined using a pair of antibodies for each of the markers to be detected. One of said pairs of antibodies is referred to herein as a "detector antibody" and the other of said pair of antibodies is referred to herein as a "capture antibody". One embodiment of the present disclosure thus uses the double antibody sandwich method for detecting PAMG-1 in a sample of vaginal fluid. In this method, the analyte is sandwiched between the detector antibody and the capture antibody, the capture antibody being irreversibly immobilized onto a solid support. The detector antibody would contain a detectable label, in order to identify the presence of the antibody-analyte sandwich and thus the presence of the analyte.

Common early forms of solid supports include plates, tubes or beads of polystyrene, all of which are well known in the field of radioimmunoassay and enzyme immunoassay. More recently, a number of porous materials such as nylon, nitrocellulose, cellulose acetate, glass fibers and other porous polymers have been employed as solid supports.

Thus, in a specific embodiment, the device of the disclosure comprises means for conducting an immunochromatographic assay ("immunochromatographic assay device"). Such a device comprises a solid phase means for conducting a liquid. As used herein, the term "solid phase means for conducting a liquid" refers to a solid support that allows migration of a liquid therethrough, e.g., via capillary action. A typical product of this nature is a nitrocellulose membrane, which may be prepared by methods well known to those skilled in the art.

Many immunochromatographic assay means and formats are known in the art, and can be used in the practice of the methods disclosed herein. Immunochromatographic assays using a membrane as a solid support in a dipstick or flow-through device are well established for use in the clinical laboratory and for alternative, i.e., non-laboratory, site testing. The usual presentation for an immunochromatographic assay device is a membrane (cellulosic or non-cellulosic) enclosed in a plastic holder. The plastic holder keeps the membrane in a suitable configuration in order to ensure correct functioning of the entire device. There are many variations of the basic structure of assay devices. For example, Litman et al. (U.S. Pat. Nos. 5,156,952 and 5,030,558) describe an assay method and device for determining the presence of a minimum amount of an analyte in a sample. Ullman et al. (U.S. Pat. Nos. 5,137,808 and 4,857,453) describe a device to house an assay membrane that includes self-contained liquid reagents to aid sample flow. Dafforn et al. (U.S. Pat. No. 4,981,768) describes a device with ports for applying sample and extra liquid. Corti et al. (European Patent Application No. 89118378.2), Greenquist et al. (U.S. Pat. No. 4,806,312) and Berger et al. (U.S. Pat. No. 5,114,673) also describe assay devices.

Preferably, the immunochromatographic assay means includes a control to indicate that the assay has proceeded correctly. The control can be a specific binding reactant at a spot more distal from the sample application point on the solid phase support than the detection zone that will bind to a labeled reagent in the presence or absence of analyte, thus indicating that the mobilizable receptor has migrated a sufficient distance with the liquid sample to give a meaningful result.

Suitable labels for use in immunochromatographic assays include enzymes, fluorophores, chromophores, radioisotopes, dyes, colloidal gold, colloidal carbon, latex particles, and chemiluminescent agents. When a control marker is employed, the same or different labels may be used for the receptor and control marker.

One embodiment of the present disclosure uses a flow-through type immunoassay device. Valkirs et al. (U.S. Pat. No. 4,632,901) discloses a device comprising an antibody, specific to an antigen analyte, bound to a porous membrane or filter to which is added a liquid sample. As the liquid flows through the membrane, target analytes bind to the antibody. The addition of the sample is followed by the addition of a labeled antibody. The visual detection of the labeled antibody provides an indication of the presence of the target analyte in the sample.

Another example of a flow-through device is disclosed by Kromer et al. (EP-A 0 229 359), which describes a reagent delivery system comprising a matrix saturated with a reagent or components thereof dispersed in a water soluble polymer for controlling the dissolution rate of the reagent for delivery to a reaction matrix positioned below the matrix.

In migration type assays, the solid phase support, e.g., membrane, is impregnated with the reagents needed to perform the assay. An analyte detection zone is provided in which labeled analyte is bound and the results of the assay are read. For example, see Tom et al. (U.S. Pat. No. 4,366,241), and Zuk (EP-A 0 143 574). Migration assay devices usually incorporate within them reagents that have been attached to colored labels such as colloidal gold or carbon, thereby permitting visible detection of the assay results without addition of further substances. See for example, Bernstein (U.S. Pat. No. 4,770,853), May et al. (WO 88/08534), and Ching et al. (EP-A 0 299 428). All of these known types of flow-through devices can be used according to the methods disclosed herein.

Direct labels are one example of labels that can be used in immune-chromatographic assays according to the present disclosure. A direct label has been defined as an entity, which in its natural state, is readily visible, either to the naked eye, or with the aid of an optical filter and/or applied stimulation, e.g., U.V. light, to promote fluorescence. Examples of colored labels that can be used according to the present disclosure, include metallic sol particles, for example, gold sol particles such as those described by Leuvering (U.S. Pat. No. 4,313,734); dye sol particles such as described by Gribnau et al. (U.S. Pat. No. 4,373,932) and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionuclide, a fluorescent moiety or a luminescent moiety. In addition to these direct labeling devices, indirect labels comprising enzymes can also be used according to the present disclosure. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in Methods in Enzymology, 70. 419-439, 1980 and in U.S. Pat. No. 4,857,453.

In a specific embodiment, the diagnostic device of the present disclosure comprises a membrane assembly having a detection section proximal to the point of introduction of the sample, and a capture section downstream from that position. The detector section contains antibodies (detector antibodies) (e.g., monoclonal antibodies), which will react with any analytes of the present disclosure that are present in the sample. The detector antibodies are reversibly immobilized onto the membrane and will migrate with the sample, when in use. It is preferred although not essential, that the detector antibodies are labeled, for example, with a radionuclide, an enzyme, a fluorescent moiety, luminescent moiety or a colored label such as those described in the prior art, and discussed above. Specifically, one could employ a reactive label, so that for example, the antibody would appear gold before capture of the antigen, and would change to purple upon capture.

The capture section which, as stated, is downstream from the detector section, comprises capture antibodies (e.g., monoclonal antibodies), which are irreversibly immobilized onto the solid support, each antibody immobilized at a different position in the capture section. The antibodies and necessary reagents are immobilized onto the solid support using standard art recognized techniques, as discussed in the flow-through type immunoassay devices discussed previously. In general, the antibodies absorbed onto the solid supports as a result of hydrophobic interactions between non-polar protein substructures and non-polar support matrix material.

A particular advantage of the immunochromatographic assay technology of the present disclosure is that it overcomes the inability of these assays to provide quantitative data. Thus, the capture section can contain a mixture of immobilized antibodies specific for PAMG-1, such that a signal is only produced when the amount of PAMG-1 in the sample exceeds the desired detection threshold.

In addition, the present disclosure contemplates use of homogeneous immunoassay formats. One example of such a competitive homogeneous method is found in U.S. Pat. No. 3,817,837 by Rubenstein and Ullman, which describes a technique in which ligand and enzyme-bound-ligand compete for antibody binding sites. Since binding of the antibody to the enzyme-bound-ligand alters its enzymatic activity, the concentration of ligand present can be estimated by measuring the rate at which such a mixture converts substrate to product. Thus, in a homogeneous method, the detectable property of the label is inherently different depending on whether bound or unbound. In its bound state, the label will have greater or lesser signal intensity. Usually, binding of antibody to the labeled ligand causes a decrease in signal intensity, e.g., when the label is an enzyme. Typical products in this category include the EMIT line of enzyme immunoassays from Syva Company and the TDX line of fluorescence polarization immunoassays from Abbott Diagnostics. A particular homogeneous assay could be prepared with the disposition of all of the analytes on beads, in which event the sample would be introduced and the beads thereafter spun down and detected.

Other examples of biological diagnostic devices that can be used according to the present disclosure include the devices described by G. Grenner, P. B. Diagnostics Systems, Inc., in U.S. Pat. Nos. 4,906,439 and 4,918,025. The Grenner '439 device comprises a diagnostic test element and a sample application unit comprising a fluid delivery element that is characterized as having a layer with a plurality of grooves for the delivery of the sample to the test element. Grenner '025 relates to a device that includes a sample introducing means such as a membrane adjacent to which is positioned a capillary containing a fixed reagent and a waste liquid reservoir. Release of the fixed reagent from the capillary completes the reaction after the sample is deposited, and excess liquid is retained by the waste reservoir, so that the device is self-contained.

While the measurement with a membrane is preferred, it is to be understood that other techniques and corresponding sensor devices may likewise be used in similar fashion to the above. There are currently available several types of automated assay apparatus, which can undertake an assay on a number of samples contemporaneously. These automated assay apparatuses include continuous/random access assay apparatus. Examples of such systems include OPUS™ of PB Diagnostic System, Inc. and the IMX™ Analyzer introduced by Abbott Laboratories of North Chicago, Ill. in 1988. In general, a sample of the test fluid is typically provided in a sample cup and all the process steps including pipetting of the sample into the assay test element, incubation and reading of the signal obtained are carried out automatically. The automated assay systems generally include a series of workstations each of which performs one of the steps in the test procedure. The assay element may be transported from one workstation to the next by various means such as a carousel or movable rack to enable the test steps to be accomplished sequentially. The assay elements may also include reservoirs for storing reagents, mixing fluids, diluting samples, etc. The assay elements also include an opening to permit administration of a predetermined amount of a sample fluid, and if necessary, any other required reagent to a porous member. The sample element may also include a window to allow a signal obtained as a result of the process steps, typically a fluorescent or a colorimetric change in the reagents present on the porous member to be read, such as by a means of a spectroscopy or fluorimeter, which are included within the assay system. The automated assay instruments of PB Diagnostic Systems, Inc. are described in U.S. Pat. Nos. 5,051,237; 5,138,868; 5,141,871 and 5,147,609.

Further classes of immunochemical analyzer systems, which can be used in practicing the methods disclosed herein, are the biosensors or optical immunosensor systems. In general an optical biosensor is a device that uses optical principles quantitatively to convert chemical or biochemical concentrations or activities of interest into electrical signals. These systems can be grouped into four major categories: reflection techniques; surface plasmon resonance; fiber optic techniques and integrated optic devices. Reflection techniques include ellipsometry, multiple integral reflection spectroscopy, and fluorescent capillary fill devices. Fiber-optic techniques include evanescent field fluorescence, optical fiber capillary tube, and fiber optic fluorescence sensors. Integrated optic devices include planer evanescent field fluorescence, input grading coupler immunosensor, Mach-Zehnder interferometer, Hartman interferometer and difference interferometer sensors. Holographic detection of binding reactions is accomplished by detecting the presence of a holographic image that is generated at a predetermined image location when one reactant of a binding pair binds to an immobilized second reactant of the binding pair (see U.S. Pat. No. 5,352,582, issued Oct. 4, 1994 to Lichtenwalter et al.). Examples of optical immunosensors are described in general in a review article by G. A. Robins (Advances in Biosensors), Vol. 1, pp. 229-256, 1991. More specific descriptions of these devices are found for example in U.S. Pat. Nos. 4,810,658; 4,978,503; and 5,186,897; R. A. Brady et al. (Phil. Trans. R. Soc. Land. B 316, 143-160, 1987) and G. A. Robinson et al. (in Sensors and Actuators, Elsevier, 1992).

The methods and corresponding kits of the present disclosure are capable of incorporation and practice within a variety of optical measurement systems. Specifically, while the kits and materials of the present disclosure may be practiced in an immunoassay format, such format itself is capable of embodiment in a variety of optoelectronic detection systems. More particularly, a variety of optical immunosensor technologies are already known that may be facilitated and implemented in the practice of the methods disclosed herein. Thus, for example, devices and techniques such as reflection techniques, surface plasmon resonance, fiber optic waveguide techniques and integrated optic devices, may all be adopted and specifically configured to detect and display the results of the examination of a patient's biological sample in accordance with the present method. Particular reflection techniques, such as reflectometry and ellipsometry, and the specific use of optical fibers, optical waveguides, fluorescent capillary fill devices and integrated optical biosensors, present but a few of the variant techniques and equipment that may be employed. A general review of these devices may be found in Robinson, G. A., Optical Immunosensors: An Overview, Advances in Biosensors, Vol. 1, pp. 229-256 (1991).

More particularly, ellipsometry relies on the direction of a polarized light beam first against a reference surface (a standard) and thereafter against the sample surface, following which a comparison of the nature and extent of the resulting reflections can be made. Particularly, the binding of analyte to receptor molecules will be measured as a change in the thickness of the surface relative to the reference surface.

In the instance of multiple internal reflection spectroscopy, for example, the ligand and its receptor may be covalently immobilized on the optical surface of a planar, fused-quartz waveguide after which a light beam may be internally reflected within the waveguide and would penetrate into a solution adjacent the waveguide, so that refractive differences would be capable of measurement as between the standard and the sample. In this particular format, a fluorescent label may be associated and measurements of fluorescence resultantly taken to determine the present extent of binding.

An additional technique utilizes the technology known as fluorescent capillary fill device. In this particular technology, two glass plates held apart by a gap of capillary dimension are utilized. Receptor molecules may be immobilized onto the base plate, which also acts as an optical waveguide.

Competitive or sandwich assays utilizing FITC labeling may be performed and induced fluorescence is coupled into the waveguide with a signal from bound as opposed to unbound sources. Such signal is discriminated by its angular divergence upon exiting the waveguide. Surface Plasmon Resonance (SPR) devices have also been prepared which operate in response to the coupling of light incident upon a thin metal film into surface modes associated with collective electron oscillations within the metal film. Resonance condition is dependent upon the optical characteristics of the metal film, its thickness, the refractive indices of the dielectric on either side of it, and the angle of incidence of light. Receptor molecules are bound to the top side of the metal film, and the light is directed at the bottom side of the film, such as through a prism substrate. The target analyte, when binding to these receptors, will cause a shift in the resonance condition because of the change it produces in the local refractive index. Resonance is observed by a monitoring of the reflected light intensity as the angle of incidence at the light beam on the metal film surface varies. The change in resonance angle will directly correlate with the amount of analyte bound.

The techniques involving fiber optic systems include the evanescent field fluorescence. In this instance, the cladding is removed from the end of an optical fiber, thus producing a sensor element that evanescently interacts with the surrounding medium. Receptor molecules are bound to the exposed fiber surface, and direct assays may be performed utilizing the natural fluorescence of the receptor and conjugate proteins. Competitive or sandwich assays may be performed using FITC labeling to achieve greater sensitivity. In operation, a light wave is coupled into the fiber, and a portion of the evanescently produced fluorescence is coupled back into the fiber and propagated back to a detector.

A further technique utilizing optical fiber technology involves the optical fiber capillary tube, in which a bare fiber optic is enclosed within a cylindrical fill chamber, producing a sensor element that interacts evanescently with the portion of the fill volume immediately surrounding the fiber. Receptor molecules may be bound to the exposed fiber surface and sandwich or competitive displacement assays may be performed. A light wave would be coupled into the fiber, and a portion of the evanescently induced fluorescence would be coupled back into the fiber and propagated back to a detector. The signal from the target analyte versus the background sources is discriminated by its angular divergence upon exiting the fiber. Other fiber optic techniques such as fiber optic fluorescence may be adapted to the methods disclosed herein utilizing certain of the same principles enunciated above.

Further photonic techniques such as interferometry include the disposition of a thin-film waveguide having, for example, two paths, on the first of which receptor molecules may be immobilized while the second is shielded to provide a reference channel. Laser light, for example, may be coupled into the waveguide and split down the two paths, so that changes in the refractive index and thickness of the covering letter may be detected by the result of a phase shift in the beam, which will, in turn, correlate with the amount of analyte bound. A variation on this approach is identified in the Hartman interferometer, where a single path multimode thin film planar waveguide is prepared. Receptor molecules may be immobilized on this path, and light from a laser may be coupled into the waveguide so that two modes propagate down the path. The optics of multimode geometries are such that the higher order mode has a large evanescent field, providing a signal mechanism, and the lower order mode has practically no evanescent field, providing a reference mechanism. Binding with the target analyte will cause related changes in the refractive index and thickness of the covering layer over the path which will be detected by the evanescent field of the higher order mode, causing a phase shift in that mode. As the lower order or reference mode is blind to such changes, no phase shift will be experienced, and the measured difference between the signal and reference beams will be capable of correlation to determine the amount of analyte bound.

While the foregoing discussion has provided both in general terms and some detail, various techniques available in optical sensor technology are adaptable to the practice of the present disclosure. It is to be understood that the above recitation is by no means exhaustive or limitative, as a variety of extant technologies may be adopted, that will successfully measure differences in binding and, consequently, the presence and amount of the respective markers or analytes of interest herein. Of course, as emphasized above, no matter what technology is employed, the practice of the methods disclosed herein comprises simultaneous detection and measurement of at least three analytes.

Immunochromatographic Methods for Detecting PAMG-1

Embodiments of the methods of detecting PAMG-1 according to the present disclosure are described below.

In one embodiment of the method, PAMG-1 is detected in a sample through the contact of a sample containing PAMG-1 with an immunoassay system according to the methods disclosed herein to form an antibody-PAMG-1 complex. The antibody-PAMG-1 complex is then detected. In one variation of this embodiment, the antibody includes a detectable marker, the step of detecting the antibody-PAMG-1 complex, which includes the detectable marker.

In another embodiment of the method, PAMG-1 is detected in a sample by putting the sample in contact with an antibody which has a highly specific binding affinity for PAMG-1 (like M271, exemplified infra), thus forming the antibody M271-PAMG-1 complex. The complex then comes into contact with an immobilized second antibody (e.g., like M52). The second antibody is immunologically distinct from the first antibody (e.g., binds to a different epitope), so that such antibodies can simultaneously bind to the PAMG-1 molecule. The immobilized antibody binds to the mobile antibody PAMG-1 complex to form the immobilized antibody PAMG-1 antibody complex. PAMG-1 is detected by detecting this heterotrimer complex. As noted above, the antibody with high specificity for PAMG-1 is preferably used for the initial recognition of PAMG-1.

When the above-described method includes the use of one antibody of the selected pair labeled with a detectable marker, a variation of the method includes putting the sample in contact with the first, labeled antibody prior to contact of the sample with the second, immobilized antibody. In this variation, the labeled antibody serves to bind to PAMG-1 in the sample. Yet another embodiment of the method includes the following steps: adding a fluid sample containing PAMG-1 to a mobilizable, labeled antibody region of porous material which permits migration of antibodies and proteins therethrough, the antibody region including a mobilizable antibody which has a high specificity for PAMG-1 resulting in the attachment of the antibody to PAMG-1 to form an antibody PAMG-1 complex; migration of the complex to the test region containing a second antibody immobilized therein, which second antibody has a binding affinity for PAMG-1 resulting in the second antibody binding to the labeled antibody-PAMG-1 complex to form an immobilized complex; and detecting the immobilized complex in the test region.

Yet another embodiment of the method is a standard sandwich assay, in which an unlabeled antibody is immobilized on any surface. Addition of fluid sample containing PAMG 1 results in binding of PAMG-1 by the immobilized antibody to form an antibody PAMG-1 complex. Addition of labeled antibody results in formation of an immobilized complex composed of immobilized antibody PAMG-1-labeled antibody and detection of this complex.

According to the above-described methods, the antibodies may include a detectable marker or label, the step of detecting the antibody-PAMG-1 or PAMG-1-antibody complex including detection of the detectable marker or label. Examples of detectable markers that can be used include stained particles, enzymes, dyes and radioactive isotopes. In a specific embodiment, the detectable marker is a stained particle of gold, e.g., having an average dimension between about 20 nm and 30 nm. In yet another embodiment, the detectable marker is horseradish peroxidase.

Exemplary Devices for Detecting PAMG-1

A variety of devices are envisioned for detecting PAMG-1 protein in a sample. Devices and/or methods according to the present disclosure preferably can detect PAMG-1 in a sample where the concentration of PAMG-1 is between about 1 ng/ml and 50 µg/ml, about 2 ng/ml and 50 µg/ml, about 3 ng/ml and 50 µg/ml, or about 4 ng/ml and 50 µg/ml. Non-limiting examples of devices that can be used in the methods disclosed herein are described in U.S. Pat. No. 7,709,272 by Fuks et al. Devices for use in the present methods also include, e.g., a cassette containing a test strip (e.g., with a pad region where the sample is placed, and test region (where results are read)), and optionally, a built-in timer and/or a site to indicate patient identification. The pad and test regions are discussed in more detail below. In certain embodiments of the present methods, the preferred detection threshold of PAMG-1 is adjusted with the assay device and collection system (e.g., kit) to be at least about 4 ng/ml by selection of the combination of the device and vaginal flocked swab. The detection threshold of 4 ng/ml is suitable for improved PPV and NPV, and a lower threshold than offered by prior systems with the device and flocked swab. Also, the methods described herein related to the IOLP can be suitable with a detection threshold of about 4 ng/ml in vaginal fluid. It is to be understood that the methods and devices of the present disclosure also encompass PAMG-1 detection thresholds of about at least 1 ng/ml, about at least 2 ng/ml, and about at least 3 ng/ml in vaginal fluid.

It should be recognized that a device may have a lower detection threshold, such as 1 ng/ml, which can be obtained by select samples applied to the device. As such, the device can detect down to 1 ng/ml. However, such samples may not be available to take advantage of the 1 ng/ml threshold. As such, the system (e.g., kit) used to detect the PAMG-1 in vaginal fluid uses a flocked swab to obtain the vaginal fluid, and then a solution is used to withdraw the PAMG-1 from the flocked swab, and then the solution is applied to the device. Now, upon completion of transfer of PAMG-1 from vaginal fluid to flocked swab to solution to device results in the ability to have a lower detection threshold of PAMG-1 at 4 ng/ml in vaginal fluid. The ability to detect PAMG-1 when present at 4 ng/ml in vaginal fluid is a significant advance over the art (e.g., over AmniSure).

The devices and methods described herein can be adapted to be used easily in a rapid and convenient manner, thereby making it possible for the devices and methods to be used in outpatient conditions. For example, the method can be incorporated into an easy-to-use device that can be operated by a patient with little or no prior experience with the device. This makes the method and device highly reliable and not very susceptible to operator error. The method can also be designed to enable a simple "yes" or "no" (or "+" or "−") determination of the presence of PAMG-1 in a sample (e.g. vaginal fluid sample).

An exemplary, non-limiting device for detecting PAMG-1 is illustrated in FIGS. 1 and 2. The procedure of selection of, e.g., a pair of PAMG-1 specific antibodies, such as, e.g., those described above, can be reproduced by an artisan of ordinary skill in the art.

As shown in FIGS. 1 and 2, an exemplary device that can be used to perform the methods disclosed herein has a strip-like body composed of several sequentially interconnected elements. More specifically, part 12 of the device comprises a pad, which contains M271 antibody region 10, in which the M271 antibodies are labeled, e.g., by stained particles SP (not shown in the drawings). Pad 12 may be made of a fiberglass tissue or any other material, which is porous and permits the migration of various particles and substances of a sample. Stained particles may comprise gold particles having an average dimension within the range of 20 to 30 nm. The M271 antibody region also contains mouse IgG immunoglobulin labeled by the same stained particles. The labeled M271 antibodies and mouse IgG immunoglobulin are introduced into the band part 10 of pad 12 by impregnating pad 12 with a solution of labeled M271 antibodies and labeled mouse IgG. The solution of M271 antibodies and mouse IgG immunoglobulin may be introduced in nitrocellulose membrane 22 using drawing pen or microdrop forming device. Connected to one end of pad 12 in its longitudinal direction are [a] nitrocellulose membrane 22, which contains a test region 14 and a control region 16. Both the test region 14 and control region 16 are arranged transversely to the device over its entire width. Test region 14 is a band portion of nitrocellulose membrane 22. Test region 14 contains M52 antibodies attached to nitrocellulose membrane 22. Control region 16 contains anti-mouse anti immunoglobulin antibodies attached to nitrocellulose membrane 22. Control region 16 crosses the entire width of strip 22. A filter paper membrane 24 is connected to the end of nitrocellulose membrane 22, which is opposite to the end of nitrocellulose membrane 22 connected to pad 12. A filter paper membrane 24 is connected to the end of nitrocellulose strip 22 in its longitudinal direction. The surface of the device is coated with special protective films 28 and 30, e.g., thin adhesive tapes specially designed for strip devices. Arrows 18 are drawn on the surface of film 28 in order to show the sample application end of pad 12. Pad 12, nitrocellulose membrane 22 and filter paper membrane 24 are attached to an adhesive rigid plastic base 26.

In the embodiment described in this section, the device includes an M271 antibody pad region 10 formed of a porous sample application matrix that permits migration of antibodies and proteins therethrough. The M271 antibody region 10 includes the M271 antibody, which is capable of highly specific binding to PAMG-1. Introduction of a fluid sample containing PAMG-1 into M271 antibody region results in the attachment of the M271 antibody to PAMG 1 to form the antibody M271-PAMG-1 complex. The device also includes a test region 14 in fluid connection with M271 antibody region 10 formed of a porous material which permits migration of antibodies and proteins therethrough. Test region 14 includes the M52 antibody immobilized in test region 14 which is also capable of binding to PAMG-1. The M52 antibody is immunologically distinct from the M271 antibody such that the M271 and M52 antibodies can simultaneously bind to PAMG-1. Introduction of a fluid sample to the M271 antibody region 10 results in the migration of the antibody M271-PAMG-1 complex into the test region 14 where the antibody M271-PAMG-1 complex binds to the M52 antibody and is immobilized in the test region by the M52 antibody. The device detects PAMG-1 in a sample based on the presence of the M52 antibody immobilized in test region 14. As a result, only PAMG-1 forms an antibody M271-PAMG-1-M52 antibody complex which is immobilized in the test region 14. Thus, the presence of the M52 antibody immobilized in the test region 14 is indicative of the presence of PAMG-1 in the sample.

In this embodiment of a device for detecting PAMG-1 in vaginal secretions, the M271 antibody is attached to a detectable marker which is used to detect PAMG-1 immobilized in the test region 14. Examples of detectable markers that may be used include, but are not limited to, stained particles, enzymes, dyes, fluorescent dyes, and radioactive isotopes. In one embodiment, the detectable marker is gold particles having an average dimension between about 20-30 nm. In one embodiment, the M271 antibody is a labeled antibody in a freeze-dried state.

In a variation of the embodiment where the M271 antibody in the M271 antibody pad region is labeled with a detectable marker, the device further includes a test region, which contains the M52 antibody. The pad region and test region are in fluid connection.

In yet another embodiment of the device, also embodied within the device illustrated in FIGS. 1 and 2, the device has a strip-like body with proximal and distal ends. The M271 antibody region 10 of the strip-like body is made of a material which permits the migration of antibodies and proteins therethrough. The M271 antibody region 10 of the strip-like body includes the M271 antibody, which has a highly specific binding affinity for PAMG-1, introduction to the M271 antibody pad region of a fluid sample containing PAMG-1, which results in the attachment of the M271 antibody to PAMG-1 to form the antibody M271-PAMG-1 complex.

The strip-like body also includes a test region 14, which is proximal to the M271 antibody region 10 and is in fluid connection with the M271 antibody region 10. The test region 14 is formed of a material which permits migration of antibodies and proteins therethrough. The test region 14 includes the M52 antibody immobilized in the test region 14, which has a binding affinity for PAMG-1, the introduction of the fluid sample to the M271 antibody region 10 resulting in the migration of the antibody M271-PAMG-1 complex to the test region 14 where the antibody M271-PAMG-1 complex binds to the M52 antibody and is immobilized in test region 14 by the M52 antibody. The test region can also include M42 antibody and M52 antibody immobilized in the test region 14. The device detects PAMG-1 in a sample based on the immobilization of the complex of labeled antibody M271-PAMG-1 in the test region 14. Using various combinations of PAMG-1 specific antibodies (e.g., M42 and M52) immobilized in the test region exemplifies one way to adjust the sensitivity threshold (detection threshold) of the strip device (see U.S. Pat. No. 7,709,272 by Fuks et al.). However, the artisan of ordinary skill in the art will appreciate that other methods of adjusting the detection threshold are possible (e.g., varying the binding affinity of the immobilized and immobilizable antibodies of a pair of PAMG-1 specific antibodies and/or adjusting the procedure, e.g., the procedural timing of the steps of the testing procedure, as disclosed herein).

The device can include a standard control region 16 (FIGS. 1 and 2). This control region serves to confirm the proper operation of the device. However, any alternative control region designs may also be used with a device for use in the methods disclosed herein. For example, a device with one control region can include the M271 antibody region 10 formed of a material which permits migration of antibodies and proteins therethrough, the M271 antibody region 10 including a labeled M271 antibody that is not immobilized therein and has a high specificity for PAMG-1, and introduction to the M271 antibody pad region 10 of a fluid sample containing PAMG-1 resulting in the M271 antibody binding to PAMG-1 to form an antibody M271-PAMG-1 complex. The device can also include a test region 14 in fluid connection with M271 antibody region 10 which is formed of a material which permits migration of antibodies and proteins therethrough. The test region 14 also includes the M52 antibody immobilized in the test region 14 which has a binding affinity for PAMG-1. The M52 antibody is immunologically distinct from the M271 antibody such that the M271 and M52 antibodies can simultaneously bind to PAMG-1. Introduction of the fluid sample to the M271 antibody region 10 results in the migration of the antibody M271-PAMG-1 complex into the test region 14 where the antibody M271-PAMG-1 complex binds to the M52 antibody and is immobilized in test region 14 by the M52 antibody. The device detects PAMG-1 in a sample based on the immobilization of the labeled M271 antibody in the test region 14. When a low concentration of PAMG-1 is present in the sample, at least some of the labeled M271 antibodies migrate from the M271 antibody region 10 through the test region 14 to the control region 16. Anti-mouse anti-immunoglobulin antibodies are immobilized in the control region 16. Anti-immunoglobulin antibodies bind labeled M271 antibodies that stain the control region. If a high concentration of PAMG-1 is present in the sample, then only a low quantity of labeled M271 antibodies can approach the control region 16 and coloration of the control region may be too weak to become visible to the naked human eye. To prevent such a possibility, labeled mouse IgG immunoglobulin was added into M271 antibody region 10. This immunoglobulin does not bind PAMG-1 and migrates freely through M52 antibody test region 14 to the control region 16 where it is bound by anti-mouse antiglobulin antibodies and stains control region 16. The control region confirms the proper functioning of the device regardless of the concentration of PAMG-1 in the sample.

Yet another component of the device can be a porous material that is in tight porous connection with material of test region. This part of the device works as a pump that helps to move liquids, proteins and antibodies therethrough. Examples of detectable markers, which may be used for the labeling of mouse antibodies and IgG immunoglobulin include, but are not limited to stained particles, enzymes, dyes, and radioactive isotopes. In one embodiment, the detectable marker is a fluorescent dye. In yet another embodiment, the detectable markers are stained particles. In one embodiment, the M271 antibody, which is a labeled antibody and the labeled mouse immunoglobulin IgG are in a freeze-dried state.

The materials used in the various regions of the above-described device may be any combination of materials that permit the migration of antibodies and proteins therethrough. Examples of suitable materials include but are not limited to fiberglass, porous plastic, nitrocellulose, and filter paper.

The parts of a device for use in a method disclosed herein can be positioned in any functional combination (e.g., in a lateral flow device, cassette, etc.) provided that PAMG-1 can be detected in the sample when present at a concentration of at least a predefined detection threshold (e.g., 4 ng/ml).

Devices for use in the present methods may optionally include a protective film covering at least a portion of the device. It can be transparent or not transparent and can have necessary trademark, informational marks/signs or arrows on its surface.

Sample Collection

In the methods disclosed herein, it is necessary to collect a vaginal fluid sample from a patient. The device or tool or other means used to collect the sample, and transfer the sample to solution (for testing), can be varied according to the present disclosure, so long as the sample is collected. Non-limiting examples of devices for collecting vaginal fluid sample (e.g., a vaginal fluid sample containing PAMG-1), include, e.g., vaginal swabs (e.g., flocked vaginal swabs).

Figure 3:
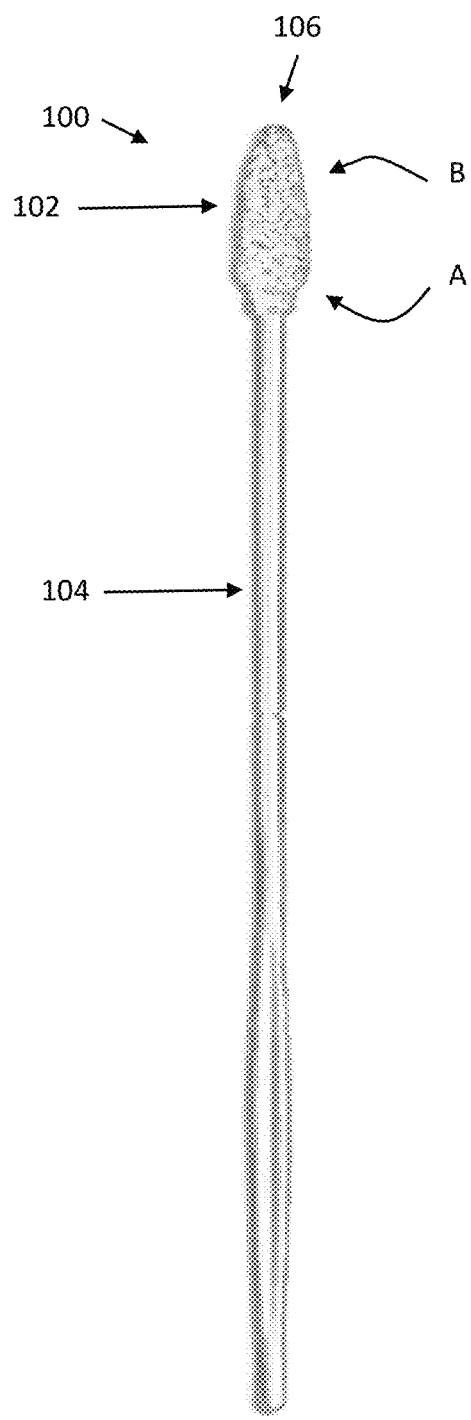
FIG. 3 illustrates an example of a flocked swab.

In one aspect, the flocked swab can be a Copan FLOQSwab, such as exemplified in FIG. 3, which can be a nylon flocked swab. In one aspect, the flocked swab 100 can have a swab head 102 shape as shown in FIG. 3. In one aspect, the flocked swab 100 can have a shape as shown in FIG. 3, where the shaft 104 is elongate with the swab head 102 being wider at the point (A) where the shaft 104 is inserted therein, and with a tapered shape that tapers (B) from the initially wide portion (A) toward the tip 106. The head can be wide at the base (e.g., opposite of the tip) with a generally conical shape that tapers down to the tip. The tip can have a flattened end. The flocked vaginal swab with the following specifications: length of the plastic shaft: 170.0 mm±1 mm; plastic tip diameter: 4.6 mm±0.1 mm; stick diameter handle part: 4.4 mm±0.2 mm; length of the fiber tip: 22 mm±3 mm; flocked tip diameter (e.g., widest part of cone shape): 7.00 mm±1.5 mm; total length: 171 mm±2 mm, where any dimension can independently be +/−1%, 2%, 5%, 10%, 20%, 25%, 50%, 75%, or 100%.

Non-limiting examples of other means to collect a vaginal fluid sample include, e.g., douche method or vaginal wash. Also, a syringe may be used to collect the vaginal fluid sample.

The specific device and/or method of sample collection can be varied, and any suitable device or method known in the art can be used, so long as the vaginal fluid sample is successfully collected. Preferably, the device or means of sample collection yields at least 70%, at least 75%, at least 80%, at least 85%, at least 90%, at least 95%, or greater of the target analyzed in the sample (e.g. PAMG-1). For example, the flocked vaginal swab used in the present examples yields about 80-90% of the PAMG-1 after collection and transfer to solution, where the solution can be applied to the device.

In certain embodiments, the device or means used to collect the vaginal fluid sample provides a 1:1, 1:2, 1:3, 1:4, 1:5, 1:6, 1:7, 1:8, 1:9, or 1:10 dilution of the vaginal fluid sample. In certain embodiments, the device of or means used to collect the vaginal fluid sample provides a dilution of the vaginal fluid sample in the range of 1:1 to 1:10, 1:2 to 1:9, 1:2 to 1:8, 1:2 to 1:7, 1:2 to 1:6, 1:2 to 1:5, 1:2 to 1:4, 1:2 to 1:3, 1:3 to 1:10, 1:3 to 1:9, 1:3 to 1:8, 1:3 to 1:7, 1:3 to 1:6, 1:4 to 1:7, or 1:5 to 1:6.

In a specific embodiment, a vaginal swab provides about a 1:4 dilution of the vaginal fluid sample. In another embodiment, a flocked vaginal swab provides about a 1:4 dilution of the vaginal fluid sample.

Kits

The present disclosure also provides kits. In one aspect a kit disclosed herein comprises a device, e.g., as disclosed herein (e.g., a lateral flow device) for detecting the presence of PAMG-1 in a sample when present at a level above a predetermined detection threshold (e.g., 0.5 ng/ml, 1 ng/ml, 2 ng/ml, 3 ng/ml, or 4 ng/ml). In another aspect a kit disclosed herein comprises a device (such as, but not limited to a lateral flow device, e.g., such as a device similar to one described in U.S. Pat. No. 7,709,272) for detecting the presence of PAMG-1 in a sample when present at a level above a predetermined threshold (e.g., 0.5 ng/ml, 1 ng/ml, 2 ng/ml, 3 ng/ml, or 4 ng/ml); and a means for collecting a vaginal fluid sample (e.g., a vaginal swab, such as, but not limited to, a vaginal swab described herein such as a flocked vaginal swab, a syringe, a douche kit, or other suitable device for collecting the sample). In certain aspects, the means for collecting the vaginal fluid sample can optionally be used to dilute the vaginal fluid sample (e.g., 1: 1, 1:2, 1:3, 1:4, 1:5, 1:6, 1:7, 1:8, 1:9, 1:10, or, e.g., in a range of 1:1 to 1:10, 1:2 to 1:9, 1:2 to 1:8, 1:2 to 1:7, 1:2 to 1:6, 1:2 to 1:5, 1:2 to 1:4, 1:2 to 1:3, 1:3 to 1:10, 1:3 to 1:9, 1:3 to 1:8, 1:3 to 1:7, 1:3 to 1:6, 1:4 to 1:7, or 1:5 to 1:6, etc.), such as the vaginal flocked swab and transfer solution can dilute with application to the device having the antibodies. The kits can also comprise a solvent for transferring the vaginal fluid sample (e.g., containing an analyte, e.g., PANIG-1), e.g., a solution containing: 0.9% NaCl, 0.01% Triton™ X100 non-ionic surfactant (Millipore Sigma), 0.05% NaN$_3$). The solvent can be contained within a vial that can also be used as an applicator of the solvent plus vaginal fluid sample, or can be applied directly onto a lateral flow device. A kit can also comprise a cassette containing a test strip (e.g., with a pad region where the sample is placed, and test region (where results are read)), and optionally, a built-in timer and/or a site to indicate patient identification. The kits disclosed herein can further comprise one or more vials (e.g., plastic vial) and/or instructions for use. For example, instructions for use can include directions for determining suitability for IOLP and/or effectiveness of IOLP, or both based on the results of the test. The kits may also include instructions for actions based on the results of positive or negative PANIG-1 or amount thereof, which actions can call for retesting, performance of IOLP, performance of IOLP at least one additional time, recommendation to avoid IOLP, recommendation to proceed to labor and delivery without IOLP, or any other. The kits can also comprise a desiccant as well as a timer, e.g., built in to the test device, or as a separate unit. The kits can comprises a device as illustrated in FIGS. 1 and 2 as well as swab of FIG. 3.

In one embodiment, the methods and kits disclosed herein are for determining whether or not a pregnant woman is a candidate for the IOLP, and can be used to collect specimens (vaginal fluid samples) from patients that do not present any signs, symptoms or complaints suggestive of labor. The patient may be close to, at, or past the due date for delivery. Preferably, the specimen is collected prior to digital examination or lubricants, and prior to use of any disinfectant solutions or medicines or 6 hours after their removal.

The specimen can be collected gently in the presence of non-significant blood admixtures, and obtained in a way not to disturb tissue in the vaginal canal or brush the vaginal canal in any way. The swab may be gently inserted into a depth into the vaginal canal, left for a determined amount of time, and then gently withdrawing the swab, without any brushing, scraping or other rough action. The methods disclosed herein can be performed even with trace amounts of blood on the collection device (e.g., swab), but no blood is preferred. The blood may be from some other issue than the collection device injuring the vaginal canal. The specimen can also be collected if urine, semen or vaginal infections are present, and can be collected from patients from 20 to 36 weeks, 6 days, gestational age, or after 36 weeks up to or after 40 weeks. Further, speculum examination is not required.

In one embodiment, the methods and kits disclosed herein are for determining whether or not the IOLP that was performed on a pregnant woman was successful can be used to collect specimens (vaginal fluid samples) from patients that have undergone the IOLP. The woman may not present any signs, symptoms or complaints suggestive of labor. However, in some instances the woman will present some signs, symptoms or complaints suggestive of labor being imminent.

In one embodiment, the methods and kits disclosed herein can be used to collect specimens (vaginal fluid samples) from patients presenting with signs, symptoms or complaints suggestive of not being ready or capable of labor, whether or not the patient has undergone an IOLP. In some instances the patient has undergone an IOLP. Preferably, the specimen is collected prior to digital examination or lubricants, and prior to use of any disinfectant solutions or medicines or 6 hours after their removal. The specimen can be collected in the presence of non-significant blood admixtures. The methods disclosed herein can be performed even with trace amounts of blood on the collection device (e.g., swab). The specimen can also be collected if urine, semen or vaginal infections are present, and can be collected from patients from 20 to 36 weeks, 6 days or after 36 weeks up to 40 weeks or 41 weeks or 42 weeks of gestation or longer. Further, speculum examination is not required but can be performed.

In one embodiment, the methods and kits disclosed herein can be used to collect specimens (vaginal fluid samples) from patients that have undergone an IOLP. In some instances the patient has undergone an IOLP within 2, 4, 6, 8, 10, 12, 14, 16, 18, 20, or 24 hours earlier, but up to 36 and 42 hours earlier, or longer in some instances. Preferably, the specimen is collected prior to digital examination or lubricants, and prior to use of any disinfectant solutions or medicines or 6 hours after their removal. The specimen can be collected in the presence of non-significant blood admixtures. The methods disclosed herein can be performed even with trace amounts of blood on the collection device (e.g., swab). The specimen can also be collected if urine, semen or vaginal infections are present, and can be collected from patients from any women that has had an IOLP. Further, speculum examination is not required but can be performed.

The following methods for collecting a vaginal fluid sample from a pregnant woman and assaying the sample for the presence of PAMG-1 according to the present disclosure can be used. Although the skilled artisan will appreciate that different methods and/or test devices can be used to achieve the same results, as disclosed herein, and are also encompassed by the present disclosure.

Sample Collection

In one example of a test according to the present methods, a sample of cervicovaginal discharge collected by vaginal swab (e.g., nylon flocked) is extracted into a solvent as follows: Take the solvent (e.g., containing: 0.9% NaCl, 0.01% Triton™ X100 non-ionic surfactant, Millipore Sigma, 0.05% $NaN_3$) vial by its cap and shake well to make sure all liquid in the vial has dropped on the bottom. Open the solvent vial and put it in a vertical position. To collect a sample from the surface of the vagina, a vaginal swab can be used (e.g., a sterile flocked swab), or other suitable collection device or means to collect the vaginal fluid sample, as disclosed above. For the vaginal swab, the swab tip should not touch anything prior to its insertion into the vagina. Hold the swab in the middle of the stick and, while the patient is lying on her back, carefully insert the swab tip of the swab into the vagina until the fingers contact the skin or until the tip of the swab is no more than about 2-3 inches (5-7 cm) deep. Withdraw the swab from the vagina after about 30 seconds (other lengths of time, e.g., about 10, 20, 40, 50, 60, 90, 120 seconds, 3 minutes, 4 minutes, 5 minutes, etc.). Place the swab tip into the vial and rinse the swab in the solvent (e.g., 0.55 ml solvent) by rotating for about 30 seconds (other lengths of time, e.g., about 10, 20, 40, 50, 60, 90, 120 seconds, 3 minutes, 4 minutes, 5 minutes, etc.). Remove and dispose of the swab. The skilled artisan will appreciate that the above procedure and sample collection and transfer of sample to solvent times may vary if other device(s) and/or means or methods are used to collect the vaginal fluid sample. Other such devices and procedures and procedural timing are also encompassed by the present methods.

Test Procedure (PAMG-1 Detection)

Following transferring of the vaginal fluid sample obtained from the patient to solution (e.g., by rinsing of the swab in the solvent), contact a PAMG-1 test device, e.g., as disclosed herein, e.g., a lateral flow device, with the solvent. In one embodiment, the sample flows from an absorbent pad to a nitrocellulose membrane, passing through a reactive area containing monoclonal anti-PAMG-1 antibodies conjugated to a gold particle. The antigen-antibody complex flows to the test region where it is immobilized by a second anti-PAMG-1 antibody. This event leads to the appearance of a test line. Unbound antigen-antibody complexes continue to flow along the test strip and are immobilized by a second antibody. This leads to the appearance of an internal control line. In one embodiment, the test strip is dipped into the vial with solvent for about 5 minutes (other lengths of time, e.g., about 1, 2, 3, 4, 6, 7, 8, 9, 10 minutes, are also contemplated herein, depending upon the specific conditions of the test and the specific method or device used to test the sample). The test strip can be removed as soon as two stripes are clearly visible in the vial (about 5 minutes). The results can then be read (e.g., by placing the test on a clean, dry, flat surface). In one embodiment, the presence of two lines indicates a positive test result (PAMG-1 detected) and the presence of one line indicates a negative result. The skilled artisan will appreciate that the above procedural steps and timing are exemplary only, and are not limiting.

As discussed above, it is to be understood that variations of this procedure are also encompassed by the present disclosure, so long as they result in the detection of PAMG-1 in the vaginal fluid sample when present at a predefined detection threshold (e.g., about at least 4 ng/ml, about at least 3 ng/ml, about at least 2 ng/ml, or about at least 1 ng/ml). Thus, for example, the type and volume of solvent, device or means for sample collection, and PAMG-1 detection device can be varied or completely different from those disclosed as examples herein. The incubation times above, e.g., 30 second sample collection with swab, 30 second rinse of swab in solvent may vary depending on the specific procedure and test device used. The site of vaginal fluid sample collection can vary, and can be determined by one of ordinary skill in the art. By way of non-limiting example, exemplary sites of collection of vaginal fluid samples include collection from, e.g., cervical os, cervical canal, posterior fornix, vaginal cavity/canal. Collection of the sample can be blind (i.e., collected from the vagina without use of a speculum).

In accordance with the present disclosure, there may be employed conventional molecular biology, microbiology, recombinant DNA, immunology, cell biology and other related techniques within the skill of the art. See, e.g., Sambrook et al., (2001) Molecular Cloning: A Laboratory Manual. 3rd ed. Cold Spring Harbor Laboratory Press: Cold Spring Harbor, N.Y.; Sambrook et al., (1989) Molecular Cloning: A Laboratory Manual. 2nd ed. Cold Spring Harbor Laboratory Press: Cold Spring Harbor, N.Y.; Ausubel et al., eds. (2005) Current Protocols in Molecular Biology. John Wiley and Sons, Inc.: Hoboken, N.J.; Bonifacino et al., eds. (2005) Current Protocols in Cell Biology. John Wiley and Sons, Inc.: Hoboken, N.J.; Coligan et al., eds. (2005) Current Protocols in Immunology, John Wiley and Sons, Inc.: Hoboken, N.J.; Coico et al., eds. (2005) Current Protocols in Microbiology, John Wiley and Sons, Inc.: Hoboken, N.J.; Coligan et al., eds. (2005) Current Protocols in Protein Science, John Wiley and Sons, Inc.: Hoboken, N.J.; Enna et al., eds. (2005) Current Protocols in Pharmacology John Wiley and Sons, Inc.: Hoboken, N.J.; Hames et al., eds. (1999) Protein Expression: A Practical Approach. Oxford University Press: Oxford; Freshney (2000) Culture of Animal Cells: A Manual of Basic Technique. 4th ed. Wiley-Liss; among others. The Current Protocols listed above are updated several times every year.

The following examples are meant to illustrate, not limit, the present disclosure.

Example 1—PAMG-1 Detection Kit

A kit for the detection of PAMG-1 at a detection threshold of 4 ng/ml in vaginal fluid was prepared to include the device (which device may itself have a lower detection threshold such as 1 ng/ml, but when combined with a nylon flocked swab has a detection threshold of 4 ng/ml). The kit included a diagnostic device employing monoclonal antibodies that detect PAMG-1 present in cervico-vaginal secretions, can include the device as described in detail in U.S. Pat. No. 7,709,272 by Fuks et al. along with a flocked vaginal swab. The diagnostic device is illustrated in FIGS. 1 and 2. The diagnostic device itself can detect PAMG-1 when present at a concentration of at least 1 ng/ml in the sample. The kit also included a flocked vaginal swab with the following specifications: length of the plastic shaft: 170.0 mm±1 mm; plastic tip diameter: 4.6 mm±0.1 mm; stick diameter handle part: 4.4 mm±0.2 mm; length of the fiber tip: 22 mm±3 mm; flocked tip diameter: 7.00 mm±1.5 mm; total length: 171 mm±2 mm, where any dimension can be +/−1%, 2%, 5%, 10%, 20%, 25%, 50%, 75%, or 100%. The kit further included instructions for sample collection and the testing procedure as well as for protocols for determining whether or not PAMG-1 is detected in the vaginal fluid. The sample collection and testing procedure included a 30 second swab saturation in the vagina (a sterile speculum examination was not required), a 30 second active washing step whereby the swab just removed from the vagina was actively rotated in a solvent filled vial and a 5 minute waiting period from the time the swab was removed and the test strip was inserted if two testing lines did not appear sooner. During the test procedure, PAMG-1 present in the sample sequentially bound to monoclonal antibody conjugated with labeled particles, then to monoclonal antibody immobilized on an insoluble carrier. The in vivo sensitivity detection threshold of PAMG-1 was adjusted to 4 ng/ml using the specific sample collection and TTD test procedure described below:

Sample Collection and Test Procedure

1. Take the solvent (containing: 0.9% NaCl, 0.01% Triton™ X100 non-ionic surfactant, Millipore Sigma, 0.05% NaN$_3$) vial by its cap and shake well to make sure all liquid in the vial has dropped on the bottom. Open the solvent vial and put it in a vertical position.

2. To collect a sample from the vagina use the sterile flocked swab provided with the kit. Remove the sterile flocked swab from its package following instructions on the package. The swab tip should not touch anything prior to its insertion into vagina. Hold the swab in the middle of the stick and, while the patient is lying on her back, carefully insert the swab tip of the swab into the vagina until the fingers contact the skin, so that tip of swab is no more than 2-3 inches (5-7 cm) deep. Withdraw the swab from the vagina after 30 seconds, such as without rotating, brushing or the like.

3. Place the swab tip into the vial and rinse the swab in the solvent by rotating for 30 seconds. Remove and dispose of the swab.

4. Tear open the foil pouch at the tear notches and remove the PAMG-1 test strip.

5. Dip the white end of the test strip (marked with arrows) into the vial with solvent for no more than 5 minutes, or about 5 minutes.

6. Remove the test strip if two stripes are clearly visible in the vial (no later than 5 minutes sharp). Read the results by placing the test on a clean, dry, flat surface.

7. Do not read or interpret the results after 10 minutes have passed since dipping the test strip into the vial. If 10 minutes have passed, discard the device and perform the procedure again.

8. The presence of two lines indicates a positive test result (positive for PAMG-1 being present) and the presence of one line indicates a negative test result (negative for PAMG-1 being absent).

In summary, the test procedure can include: 30 seconds collection (in vagina), 30 seconds elution (in transfer solution), and a maximum 5 minute read time from insertion of strip (device) into transfer solution until withdrawal. That is, the swab should only be within the vagina for a maximum of 30 seconds, and then in the transfer solution for a maximum of 30 seconds. The device should only be in the transfer solution for a maximum of 5 minutes. The device should be read immediately; however, it can be read for up to 10 minutes after the time point it was dipped into the transfer solution.

In one embodiment, the method of vaginal sample collection with the swab can be performed with use of a speculum. As such, the shape and size of the conical flocked swab, as shown in FIG. 3 can enable the insertion into the vagina without any assistance from a speculum.

In one embodiment, the method of vaginal sample collection with the swab can be performed with use of lubrication. As such, the shape and size of the conical flocked swab, as shown in FIG. 3 can enable the insertion into the vagina without lubrication.

In one embodiment, the method of vaginal sample collection with the swab can be performed with use of a speculum or lubrication. As such, the shape and size of the conical flocked swab, as shown in FIG. 3 can enable the insertion into the vagina without a speculum or lubrication.

This is a significant advantage over the AmniSure system that required the swab to be in the vagina for a full minute, which is not favorable for the patient. Also, the AmniSure system required the swab to be dipped in the transfer solution for a full minute, which slows down the process, which is unfavorable for the person administering the test. Additionally, the AmniSure system required the device to be dipped into the transfer solution for a full 10 minutes, which further slowed down the process. Thus, the present kit is an advance in technology.

The following inclusion and exclusion criteria can be used to determine whether or not a pregnant woman is suitable for an IOLP. For example, women that are suitable for receiving an IOLP may have one or more of the following: women between 36 and 42 weeks of gestation (or possibly later), normal pregnancy, with 3 cm cervical dilatation, without presenting self-reported signs, symptoms or complaints suggestive of labor. Additionally, patients that may be suitable for the IOLP that may need further evaluation in addition to a positive PAMG-1 test may have one or more of: cervical dilatation>3 centimeters; suspected placenta previa; >3 weeks of gestation; overt rupture of the fetal membranes (ROM) as indicated by visualized leakage of fluid from the cervical os; no cervical cerclage in place or it has been removed; and/or heavy vaginal bleeding. However, some of these conditions, such as vaginal bleeding may remove a woman from being a candidate for IOLP. For example, women that are suitable for receiving an IOLP may not have any one or more of (e.g., if they have one or more they are not suitable): uterine contractions, with or without pain; intermittent lower abdominal pain; dull backache; pelvic pressure; bleeding during the second or third trimester; menstrual-like or intestinal cramping, with or without diarrhea; leakage from the cervical os observed via a sterile speculum examination. Women not suitable for the IOLP can also include someone that has received tocolytic medications for treatment of threatened preterm delivery prior to collection of the cervicovaginal specimens or cervical length measurements; had a digital exam prior to specimen collection; a cervical cerclage in place; and/or enrollment in a tocolytic study.

Any pregnant woman that had received an IOLP can be tested to determine effectiveness of the IOLP. This may be for when suspecting the IOLP was not effective.

In one embodiment, women having the following may be suitable for receiving the IOLP or screened for suitability: women with an uncomplicated pregnancy at term and/or term +12 days; women of South Asian and Afro-Caribbean origin women of South Asian and Afro-Caribbean origin will be offered induction of labor (IOL) at 40 weeks or past 40 weeks; and women with advanced maternal age (>40 years) at or past 40 weeks.

In one embodiment, women having the following may be suitable for receiving the IOLP or screened for suitability: women with preterm prelabor rupture of membranes (PPROM) prior to 34 weeks or up to 40 weeks or up to 42 weeks will be expectantly managed and offered IOL at or after 34 weeks gestation (or up to 40 weeks or up to 42 weeks) unless there are signs of maternal or fetal compromise prior to this gestation.

In one embodiment, women having the following may be suitable for receiving the IOLP or screened for suitability: women with PPROM between 34 and 37 weeks' gestation will be offered IOL depending on clinical and examination findings and discussion with the mother regarding risks and benefits of management options.

In one embodiment, women having the following may be suitable for receiving the IOLP or screened for suitability: women with PROM after 37 completed weeks gestation will be suitable or offered screening, or expectant management for 24 hours and then determining suitable for IOL or screening to determine suitability.

In one embodiment, women with an estimated fetal weight (EFW) below 5th percentile after 37 weeks gestation but normal amniotic fluid and Doppler results should be considered suitable for IOL at 39-40 weeks' or screened for suitability.

In one embodiment, women with fetal growth restriction (FGR) prior to 34 weeks who need delivery due to abnormal Doppler are likely to need a caesarean section (CS) unless the vaginal examination findings are favorable for delivery. However, such women may be suitable for receiving the IOLP or screened for suitability.

In one embodiment, women with FGR between 34 and 37 weeks gestation who need delivery due to abnormal Doppler or maternal complications may be suitable for IOL depending on clinical and examination findings, or may be screened for suitability.

In one embodiment, women with insulin-dependent diabetes mellitus (DM) can be considered suitable for IOL at or after 38 weeks gestation, or screened for suitability.

In one embodiment, women with gestational diabetes mellitus (GDM) controlled on diet can be suitable for IOL at 40 weeks gestation, or screened for suitability.

In one embodiment, a woman with chronic hypertension/gestational hypertension can be suitable for the IOLP or screened for suitability when: after 37 weeks if blood pressure (BP) is >160/110 mm Hg or more; or after 34 weeks if BP is >160/110 mm Hg despite treatment for chronic hypertension/gestational hypertension or any pregnancy complication.

In one embodiment, a woman with preeclampsia can be suitable for the IOLP or screened for suitability when after 37 weeks or between 34 and 37 weeks.

In one embodiment, a women with an uncomplicated dichorionic diamniotic (DCDA) twin pregnancy may be suitable for IOL at or after 38 weeks gestation, or screened for suitability.

In one embodiment, a woman with reduced fetal movements (RFM) may be suitable or screened for suitability for IOLP when: >40 weeks; >37 weeks with risk factors for placental dysfunction placental dysfunction; or presenting with repeated history of RFM.

In one embodiment, a pregnant woman with signs of infection, bleeding or spontaneous rupture of membrane (SROM) is suitable for IOLP or screening for suitability.

In one embodiment, women with previous lower segment caesarean section who choose expectant management are suitable for an IOL or screened for suitability at or after 40 weeks if there is no spontaneous onset of labor.

In one embodiment, a woman with a partner in the armed forces being deployed, bereavement or terminally ill family member or previous late stillbirth, may be screened for suitability for an IOL. Optionally, the screening is after discussing the pros and cons of elective IOL with such a woman.

In one embodiment, a woman with severe symphysis pubis dysfunction who is symptomatic despite regular analgesia and physiotherapy may be screened for suitability for an IOL after 38 weeks if they request.

Prior to a IOLP, women have a transabdominal (TA) ultrasound assessment to confirm fetal presentation, estimate fetal weight, measure amniotic fluid index and assess fetal well-being using fetal Doppler indices. A blood sample is obtained via venepuncture to check up-to-date full blood count and save a blood sample for blood grouping prior to commencing IOL. They are offered a transvaginal ultra sound (TVUS) to measure cervical length prior to digital vaginal exam (VE) to assess the Bishop Score. A computerized cardiotocography (CTG) is performed to ensure fetal well-being. Women are provided an information leaflet about IOLP and given an appointment to attend for administration of induction agent. The PAMG-1 can be analyzed for presence and/or amount in vaginal fluid.

If no PAMG-1 detected (e.g., less than detection threshold), pregnant women attend the induction suite for clinical assessment when they have a VE and administration of the induction agent (e.g., IOLP). A computerized CTG is carried out and if satisfactory, women are offered inpatient admission or outpatient management based on their indication for IOL. Women are allowed to mobilize and expectant management is continued for the next 24 hours or until they are in active phase of labor, whichever is earlier. At this point, a VE is repeated and cervical dilatation is assessed. If the cervix is favorable for artificial rupture of membranes (ARM) or if the women are already in active labor, then they are transferred to the delivery suite for further management. At any time after the IOLP, the effectiveness can be determined by measuring for the presence or amount of PAMG-1, which is optionally compared to the result of PAMG-1 prior to the IOLP.

The onset of active phase of labor is defined by commencement of 3-4 regular uterine contractions every 10 minutes each lasting for 45-60 seconds and/or a cervical dilatation of 3 cm. From this point on, a graphical record of progress in labor is maintained on the partogram and progress of labor is assessed by regular abdominal exam and VE done every 4 hours unless there are complications such as fetal distress. Once this phase initiates, there is no need to determine effectiveness of IOLP by measuring the PAMG-1.

A number of new techniques have recently been described using transperineal ultrasound assessments (TPUS) to monitor labor progress, where TPUS measurements are acquired by placing an ultrasound transducer on the patient's perineum to obtain images and take measurements. The angle of progression (AOP) is a quantitative measurement of the angle from the leading part of the fetal skull and the symphisis pubis that correlates with clinical estimation of fetal station and is useful in predicting successful instrumental delivery. The head-to-perineum distance (HPD) is a linear measurement of the distance from the leading part of the fetal skull to the perineum that correlates with fetal station and time to delivery, and is useful in predicting successful vaginal delivery in prolonged labor. A simple method based on two-dimensional ultrasound to measure sonographic cervical dilatation (SCD) has recently been reported. These tests may also be performed to determine suitability for the IOLP or for screening for suitability.

The screening for suitability for an IOLP can include any of the following in addition to measuring the PAMG-1. A TPUS will be performed along with the routine ultrasound assessment to check position of occiput, AOP, HPD and SCD. A speculum examination will be performed to obtain vaginal swabs for measurement of quantitative fFN and PAMG-1. An additional bottle of blood will also be collected and stored for future research to examine potential biomarkers of adverse outcomes. When women attend the IOLP location, they will be offered a TPUS prior to administration of the induction agent to measure AOP, HPD, SCD and check position of occiput, and optionally to test the PAMG-1.

However, it should be recognized that any woman that has had an IOLP may be studied to determine the presence or amount of PAMG-1, which can be used to determine the effectiveness of the IOLP.

In one embodiment, a woman that has had the IOLP may be studied to determine the present or amount of PAMG-1, which can be used to determine the time to induction of labor and/or time to delivery.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims. All references recited herein are incorporated herein by specific reference in their entirety. Specifically, the following references are incorporated herein by specific reference: U.S. 2014/0234987; U.S. Ser. No. 10/543,873, and U.S. Pat. No. 7,709,272 as well as EP 1608268; Canadian 2515205; Japanese 2007-523663; Australian 2004226798, New Zealand 541560, and Chinese 101103931.

The invention claimed is:

1. A method of determining suitability of a pregnant woman to be a candidate for induction of labor, the method comprising:
    obtaining a vaginal fluid sample from a pregnant woman;
    contacting the vaginal fluid sample with a PAMG-1 antibody that binds with PAMG-1, said antibody selected from the group consisting of M271, produced by hybridoma N271, deposited with the Russian National Collection of Industrial Microorganisms (VKPM) Depository and assigned accession number VKPM-93; M52, produced by hybridoma N52, deposited with the VKPM and assigned accession number VKPM-92; and M42, produced by hybridoma N42, deposited with the VKPM and assigned accession number VKPM-94;
    detecting whether the PAMG-1 antibody binds with PAMG-1 in the vaginal fluid sample to form a PAMG-1-antibody complex only when the concentration of the PAMG-1 in the sample meets or exceeds a predefined detection threshold of 4 ng/ml;
    when the PAMG-1 is detected, the pregnant woman is determined to be in a condition that is not suitable for induction of labor because PAMG-1 is detected in the vaginal sample; or
    when the PAMG-1 is not detected, the pregnant woman is determined to be in a condition that is suitable to be a candidate for induction of labor because the PAMG-1 is not detected in the vaginal sample; and
    administering an agent that causes induction of labor in the woman determined to be a suitable candidate for induction of labor.

2. The method of claim 1, further comprising determining that fetal membranes of the pregnant woman are intact; and
    if intact, determining that the pregnant woman is a candidate for induction of labor; or
    if not intact, determining that the pregnant woman is not a candidate for induction of labor.

3. The method of claim 1, further comprising:
    collecting the vaginal fluid sample from the pregnant woman with a collection device, wherein the collection device is a flocked swab; and
    contacting the collection device with a solvent to release the collected vaginal fluid sample.

4. The method of claim 1, wherein the pregnant woman having the PAMG-1 below the predefined detection threshold is suitable for induction of labor when also determined to have met one or more of the following criteria:
    having an uncomplicated pregnancy at least at term plus 7 days;
    of South Asian and Afro-Caribbean origin at least at 40 weeks gestation;
    at least 40 years old at least at 40 weeks gestation;
    having preterm prelabor rupture of membranes (PPROM) at least at 34 weeks gestation;
    having prelabor rupture of membranes (PROM) at least at 37 weeks gestation;
    an estimated fetal weight (EFW) below 5th percentile after 37 weeks gestation but normal amniotic fluid and Doppler results;
    having fetal growth restriction (FGR) at least at 34 weeks gestation;
    having insulin-dependent diabetes mellitus (DM) at least at 38 weeks gestation;

having gestational diabetes mellitus (GDM) at least at 40 weeks gestation;
having chronic hypertension/gestational hypertension at least at 37 weeks gestation;
having preeclampsia at least at 34 weeks gestation;
having an uncomplicated dichorionic diamniotic (DCDA) twin pregnancy at least at 38 weeks gestation;
having reduced fetal movements (RFM) at least at 37 weeks gestation;
having signs of infection, bleeding or spontaneous rupture of membrane (SROM);
having previous lower segment caesarean section at least at 40 weeks gestation; or
having severe symphysis pubis dysfunction at least at 38 weeks gestation.

* * * * *